US009050179B2

(12) United States Patent
Brown

(10) Patent No.: US 9,050,179 B2
(45) Date of Patent: Jun. 9, 2015

(54) POSTURE IMPROVING GARMENT

(75) Inventor: Timothy W. Brown, Newport Beach, CA (US)

(73) Assignee: Intelliskin USA, LLC, Beverly Hills, CA (US)

( * ) Notice: Subject to any disclaimer, the term of this patent is extended or adjusted under 35 U.S.C. 154(b) by 25 days.

(21) Appl. No.: 13/545,790

(22) Filed: Jul. 10, 2012

(65) Prior Publication Data

US 2013/0007946 A1 Jan. 10, 2013

Related U.S. Application Data

(63) Continuation of application No. 12/498,332, filed on Jul. 6, 2009, now Pat. No. 8,214,926.

(51) Int. Cl.
*A41D 1/00* (2006.01)
*A61F 5/02* (2006.01)
*A61F 5/01* (2006.01)

(52) U.S. Cl.
CPC .............. *A61F 5/028* (2013.01); *A61F 5/0104* (2013.01)

(58) Field of Classification Search
USPC ......................... 2/70–80, 227, 228, 239, 409; 66/171–177, 182; 266/70–80, 227, 266/228, 239, 182
See application file for complete search history.

(56) References Cited

U.S. PATENT DOCUMENTS

| 3,786,804 A | 1/1974 | Lewis |
| 4,008,350 A | 2/1977 | Crawford et al. |
| 4,116,236 A | 9/1978 | Albert |
| 4,287,885 A | 9/1981 | Applegate |
| 4,325,379 A | 4/1982 | Ozbey |
| 4,366,813 A | 1/1983 | Nelson |
| 4,445,505 A | 5/1984 | Labour et al. |
| 4,561,123 A | 12/1985 | Hull |
| 4,625,719 A | 12/1986 | Chambers |
| 4,986,263 A | 1/1991 | Dickerson et al. |
| 5,109,546 A | 5/1992 | Dicker |
| 5,201,074 A | 4/1993 | Dicker |

(Continued)

FOREIGN PATENT DOCUMENTS

| CN | 1780597 A | 5/2006 |
| WO | WO 2004/096105 | 11/2004 |

(Continued)

OTHER PUBLICATIONS

Intelliskin USA LLC, Notification of the First Office Action, CN 201080036356.0, Oct. 12, 2013, 17 pgs.

(Continued)

*Primary Examiner* — Danny Worrell
(74) *Attorney, Agent, or Firm* — Morgan, Lewis & Bockius LLP

(57) ABSTRACT

The garment is adapted to be worn by a wearer. The garment includes a main body portion. The main body portion is configured to be worn over at least a portion of the wearer's body. The main body portion includes first and second portions each defining a longitudinal axis and configured to extend toward a respective limb of the wearer so as to envelop a portion of a respective limb of the wearer. At least a portion of the first strap is releasably affixed to the main body portion, and at least a first grip layer is associated with the first portion. The first strap overlies the first grip layer. The first grip layer is configured to come into contact with a wearer's skin when the garment is worn.

18 Claims, 30 Drawing Sheets

(56) References Cited

U.S. PATENT DOCUMENTS

| | | | |
|---|---|---|---|
| 5,357,637 | A | 10/1994 | Moore |
| 5,695,452 | A | 12/1997 | Grim et al. |
| 5,823,981 | A | 10/1998 | Grim et al. |
| 5,857,947 | A | 1/1999 | Dicker et al. |
| 5,865,776 | A | 2/1999 | Springs |
| 6,176,816 | B1 | 1/2001 | Dicker et al. |
| 6,279,160 | B1 | 8/2001 | Chen |
| 6,793,641 | B2 | 9/2004 | Freeman et al. |
| 7,083,586 | B2 | 8/2006 | Simmons et al. |
| 7,143,453 | B2 | 12/2006 | Duran |
| 7,229,390 | B2 | 6/2007 | Fujii et al. |
| 7,246,381 | B2 | 7/2007 | Green |
| 7,509,822 | B2 | 3/2009 | Ishida et al. |
| 7,516,498 | B2 | 4/2009 | Torry |
| 7,631,366 | B2 | 12/2009 | Oyama et al. |
| 7,631,367 | B2 | 12/2009 | Caillibotte et al. |
| 7,861,319 | B2 | 1/2011 | Torry |
| 7,871,388 | B2 | 1/2011 | Brown |
| 8,214,926 | B2 * | 7/2012 | Brown .............. 2/228 |
| 8,245,324 | B2 * | 8/2012 | Kawasaki et al. .......... 2/227 |
| 8,296,864 | B2 * | 10/2012 | Torry .............. 2/69 |
| 8,707,463 | B2 * | 4/2014 | Orloff .............. 2/22 |
| 2004/0153017 | A1 | 8/2004 | Simmons et al. |
| 2005/0020951 | A1 | 1/2005 | Gaylord et al. |
| 2005/0197607 | A1 | 9/2005 | Brown |
| 2005/0240134 | A1 | 10/2005 | Brown |
| 2007/0067892 | A1 | 3/2007 | Oyama et al. |
| 2009/0062704 | A1 | 3/2009 | Brown et al. |
| 2009/0320180 | A1 | 12/2009 | Torry |
| 2011/0213283 | A1 | 9/2011 | Brown |
| 2011/0271415 | A1 | 11/2011 | Torry |

FOREIGN PATENT DOCUMENTS

| | | |
|---|---|---|
| WO | WO 2005/086752 A2 | 9/2005 |
| WO | WO 2005/086840 A2 | 9/2005 |

OTHER PUBLICATIONS

Intelliskin USA LLC, Patent Examination Report No. 1, AU 2010271020, Dec. 24, 2013, 3 pgs.

Brown, Notice of Allowance, U.S. Appl. No. 12/498,332, Mar. 8, 2012, 5 pgs.

Brown, Notice of Allowance, U.S. Appl. No. 12/981,407, Jun. 24, 2011, 7 pgs.

Brown, Office Action, U.S. Appl. No. 12/498,332, Apr. 5, 2011, 6 pgs.

Brown, Office Action, U.S. Appl. No. 12/498,332, Oct. 20, 2011, 6 pgs.

Definition of Intermediate from dictionary.com, Apr. 8, 2009.

International Search Report/Written Opinion, PCT/US2010/038670, Oct. 6, 2010, 8 pgs.

Intelliskin USA LLC, IPRP, PCT/US2010/038670, Jan. 10, 2012, 6 pgs.

Intelliskin USA LLC, Notification of the 2nd Office Action, CN 201080036356.0, May 27, 2014, 29 pgs.

Intelliskin USA LLC, Notification of the 3RD Office Action, CN 201080036356.0, Sep. 22, 2014, 25 pgs.

Intelliskin USA LLC, Communication Pursuant to Article 94(3) EPC, EP10729980.2, Jul. 28, 2014, 8 pgs.

* cited by examiner

POSTURE IMPROVING GARMENT

RELATED APPLICATION

This is a continuation of U.S. patent application Ser. No. 12/498,332, filed Jul. 6, 2009 now U.S. Pat. No. 8,214,926, entitled "Posture Improving Garment," which is incorporated by reference herein in its entirety.

FIELD OF THE INVENTION

The present invention relates generally to body mechanics and, more particularly, to posture improvement garments configured to be worn on a user's lower body and which are specifically adapted to improve the user's body alignment or posture through the use of sensorimotor stimulation.

BACKGROUND OF THE INVENTION

The importance of good posture is well known among health professionals. Posture generally refers to the alignment of the body and, more specifically, to the relative static and dynamic positioning of the body and its limbs. Ideally, in a body exhibiting good posture, the spine has no lateral curvature and the legs have little angulation in the knees and ankles.

The effects of poor posture are well documented and include limited range of motion wherein muscles, such as the pectoral muscles in the chest, may be permanently shortened due to a hunched-over upper body position. Other effects of poor posture include discomfort in the form of headaches at the base of the skull and pain in the shoulders, arms, and hands. Additionally, poor posture may lead to pain in the jaw due to a forward-head position, as well as decreased lung capacity due to decreased volume of the chest cavity and lungs. One of the most common consequences of poor posture is the onset of lower back pain which may increase with advancing age. Finally, a hunched-over upper body position of poor posture can add years to one's appearance.

However, by assuming good posture, gravitational forces may be more evenly distributed through the bones, ligaments and muscles of the body. Maintaining good posture is equally important during passive (static) activities such as sitting and standing, as well as during dynamic activities such as walking, running, and lifting. Theoretically, the slight S-shape of the spine that is characteristic of good posture should preferably be maintained during both static and dynamic activities. Unfortunately, our increasingly sedentary lifestyle, wherein many hours are spent sitting in front of a computer, driving an automobile, or watching television, has an adverse effect on posture. Such static activities may result in forward protrusion of the head and neck, rounding of the thoracic and lumbar spine, stretching of the spinal ligaments and also causing abnormal tilting and rotation of the pelvis. This also puts added stress on the hips, joints and other portions of the lower body. Such stretching gradually causes pain in the neck, upper back, lower back and hips and results in fatiguing of the body's muscles and ligaments. Poor posture during dynamic activities such as running and lifting results in inefficient body movements with increased stress on muscles and ligaments.

Maintaining an awareness of proper posture during static and dynamic activities may sometimes prevent overstressing of muscles and ligaments. In addition, maintaining an awareness of proper posture may train certain muscles through muscle memory such that proper posture eventually becomes a habit. However, it is sometimes difficult to maintain an awareness of proper posture during mentally challenging activities such as working at a computer, or during physically challenging activities such as participating in aggressive sports. Physical therapists may utilize postural therapy to improve the posture of a patient. Such postural therapy may include techniques such as shoulder taping and breathing exercises. Conventional chiropractic techniques may utilize body manipulation and treatment to help keep the patient's spine in alignment. However, the patient must take the time and energy to visit the offices of a physical therapist or a chiropractor in order to receive the needed postural therapy and/or chiropractic manipulation. Moreover, alternative treatments predictable therapeutic response is achieved through cutaneous nerve stimulation, is often overlooked as a method to improve the patient's posture.

As can be seen, there exists a need in the art for a device that is specifically adapted to continuously train and develop certain body muscles such that the user's posture may be improved. In addition, there exists a need in the art for a device that allows for developing such muscle training during static activities such as standing and sitting. In addition, there exists a need in the art for a device that discretely allows for developing such muscle training during dynamic activities such as walking, running and during other daily activities. Furthermore, there exists a need in the art for a device for improving the user's posture that may be progressively adjusted in accordance with changes or improvements in the user's posture over time. Finally, there exists a need in the art for a device for improving the user's posture that may be adjusted according to varying physiological parameters between users including differences in user's age, body size, muscular development and underlying pathophysiologic status.

SUMMARY OF THE INVENTION

The invention is a posture improvement garment or device that is specifically adapted to provide sensorimotor stimulation or proprioceptive awareness using a combination of gripping of the skin, pressure, torque and angle simultaneously applied to the user in order to train body muscles for proper posture through muscle memory, similar to the shirt taught in U.S. Patent Application Publication No. 2009/0062704 (referred to herein as the "'704 publication"), the entirety of which is incorporated herein by reference. The device comprises a garment designed to be worn by a user and which is adapted to envelop at least a portion of the user's lower body, including the lumbo-pelvic region, hips and at least a portion of the legs or lower extremities. This garment is preferably configured like a pair of shorts or pants.

Pressure is applied to the user's skin in order to proprioceptively stimulate cutaneous nerve receptors of the skin by configuring the garment as a relatively tight, form-fitting pair of shorts. The garment is adapted to envelop at least a portion of the user's lumbo-pelvic region, hips and at least a portion of the legs or lower extremities.

The garment may be fabricated of a stretchable, yet taut material in order to provide the desirable form-fitting feature such that specific pressure may be readily applied to the surface of the skin over specific anatomical landmarks for neuromuscular stimulation. In this regard, the garment is preferably fabricated of elastomeric material that is also preferably breathable and/or which has moisture wicking capabilities such as may be provided by a material comprised of a combination of lycra and spandex, Fabrifoam, nylon or the like.

The shorts/pants create a sensation/cue on the skin through the design that specifically bends, compresses and directs the nerve receptors in the skin (peripheral nervous system 20-80 nerve endings/square inch on skin, in muscles, tendons, joint lining, etc.) to be pulled in such a way and in such a specific direction that tells the brain to instantly relax and lengthen specific, over used, under stretched muscles while the brain simultaneously commands the opposite (front to back and/or side to side), weak, under toned, under supportive muscles to contract, tone and support the wearer's core and lower extremities. This natural reflexive response is known as reciprocal inhibition and this naturally balancing muscle stimulation system retrains the wearer's muscles every time the garment is put on to create a wearable, therapeutic short/pant that decreases muscle and joint pain, improves recovery from training, travel and injury and improves aberrant biomechanics that create muscle imbalances. In a preferred embodiment, the desired cues and responses are provided by a strap system that twists each leg in a spiral manner to rotate the leg toward where the muscles are underused and weak. Spirals and spiral physiology are naturally occurring within the human body and nature as a whole and can all be related through the Fibonacci numbers or Fibonacci structure. The Fibonacci numbers are nature's numbering system. They appear everywhere in nature, from the leaf arrangement in plants, to the pattern of the florets of a flower, the bracts of a pinecone, or the scales of a pineapple. The Fibonacci numbers are therefore applicable to the growth of every living thing, including a single cell, a grain of wheat, a hive of bees, and even humans.

The Fibonacci sequence is 1, 1, 2, 3, 5, 8, 13, 21, 34, 55, and so on. It begins with the number 1, and each new term from there is the sum of the previous two. The limit ratio between the terms is 0.618034 . . . , an irrational number variously called the "golden ratio" and/or the "divine proportion," but in this century more succinctly "PHI" (f) after the architect Phidias, who designed the Parthenon. In other words, any two adjoining numbers equal the next higher number. For example, 5+8=13. Any number divided by the next higher number gives a ratio of 0.618. For example, 8/13=0.618. Any number divided by the next lower number gives a reciprocal of 1.618.

In the lower numbers the ratios are not exact, but close enough for practical purposes. Both the Fibonacci Sequence and the Golden Ratio appear in natural forms ranging from the geometry of the DNA molecule (and the human body) to the physiology of plants and animals. In recent years, science has taken a quantum leap in knowledge concerning the universal appearance and fundamental importance of Fibonacci mathematics. Some of history's greatest minds, from Pythagoras to Isaac Newton, have held phi (f) and the Fibonacci sequence in the highest esteem and reverence.

All human senses, including hearing, touch, taste, vision and pain receptors, have not only spiral physiology, but also response curves that are logarithmic (having a Fibonacci structure). Cellular action membrane potentials, which are important for muscles and the nervous system, have a voltage equal to the log of the ratio of the ion concentration outside the cell to that of inside the cell. The brain and nervous systems are made from the same type of cellular building units and look similar microscopically, so the response curve of the central nervous system is probably also logarithmic. This spiral/helical physiology is utilized by the design of the garment of the present invention. The straps extend about the axis of the legs or feet.

The design stimulates the sensorimotor system (sensori includes the nervous system combined with the (motor) musculoskeletal system), instantly cueing a wearer's lower body into muscular balance and ideal anatomical alignment. This stimulates the user's anatomy on both a conscious and subconscious level. This instantly allows the wearer to move with more biomechanical efficiency which means using less energy while enhancing and optimizing body mechanics and gait. This has an effect that decreases normal wear and tear on joints and enhances healthy circulation and recovery from training, travel, and injury.

It will be appreciated that virtually every time a user puts the garment on, he/she is training. The garment makes weak muscles work. When a weak muscle works it helps to balance the muscles so the body is using all sides to work with rhythm and synchrony making the body move with more efficiency, greater fluidity and less effort.

In accordance with one preferred embodiment of the present invention, there is provided a garment adapted to be worn by a wearer. The garment includes a main body portion that is configured to be worn over at least a portion of the wearer's lumbo-pelvic region, hips and at least a portion of the legs. The main body portion includes first and second leg portions that each define an axis. The garment also includes at least a first strap associated with the main body portion that is releasably affixed to the first leg portion, and at least a first grip layer associated with the main body portion. The first strap overlies the first grip layer. The first grip layer is configured to come into contact with a wearer's skin when the garment is worn. In a preferred embodiment, the first strap is positioned such that it extends in a spiral about the axis of the first leg portion. In a preferred embodiment, the first and second leg portions include a stirrup extending from the bottom thereof and an adjustable arch strap attached at an upper end to the leg portion and at a lower end to the stirrup. Preferably, the stirrups each include a longitudinal arch support, a transverse arch support and a heel support.

In accordance with another preferred embodiment of the present invention, there is provided a garment adapted to be worn by a wearer. The garment includes a main body portion that is configured to be worn over at least a portion of the wearer's lumbo-pelvic region, hips and at least a portion of the legs, wherein the main body portion includes first and second leg portions that each define an axis. The garment also includes a strap system that includes a plurality of leg straps releasably affixed to the main body portion. Each of the leg straps includes at least one connector for affixing the leg strap to the main body portion. Each of the leg straps overlies a grip layer that is adapted to contact the wearer's skin when the garment is worn.

In accordance with another preferred embodiment of the present invention, there is provided a method that includes donning a garment that covers at least a portion of the wearer's lumbo-pelvic region, hips and at least a portion of the legs. The garment includes first and second leg portions that each define an axis. The method further includes positioning a first strap on the first leg portion such that it extends in a spiral about the axis of the first leg portion, thereby defining a first spiral direction. The first strap overlies a first grip layer that is in contact with the skin on the wearer's leg and the first grip layer pulls the wearer's skin in the first spiral direction.

The invention, together with additional features and advantages thereof, may be best understood by reference to the following description taken in conjunction with the accompanying illustrative drawings. In these accompanying drawings, like reference numerals designate like parts throughout the figures.

BRIEF DESCRIPTION OF THE DRAWINGS

Like numerals refer to like structures or features throughout the several views of the drawings.

DETAILED DESCRIPTION OF THE INVENTION

Figure 1:
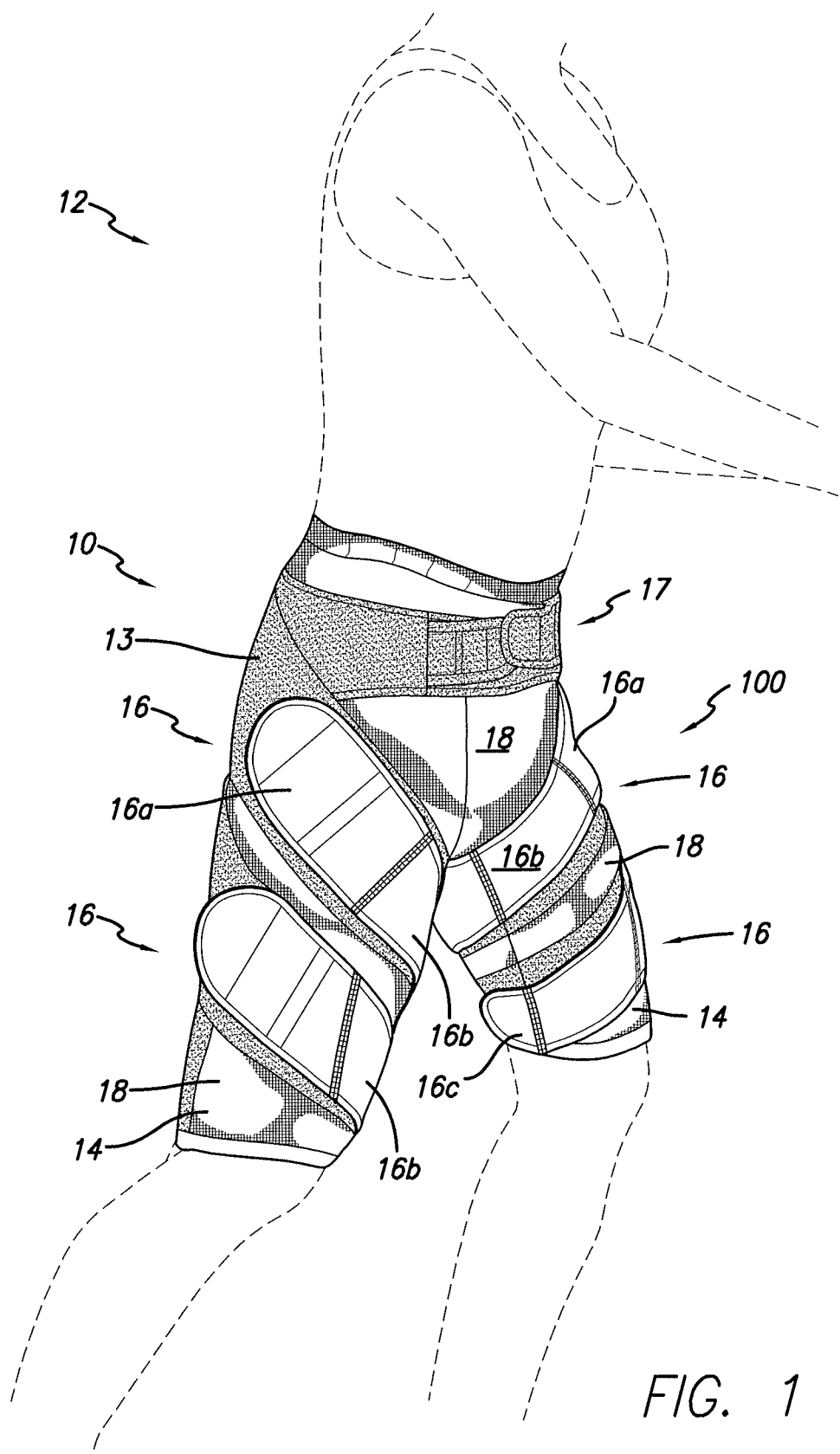
FIG. 1 a perspective view of a garment (pair of shorts) as worn by a user in accordance with a preferred embodiment of the present invention.

As shown in the drawings, for purposes of illustration, preferred embodiments of posture improvement garments (shorts 10, three quarter length pants 30, full length pants 40 and pants with stirrups 50) are shown and described. It will be appreciated that terms such as "front," "back," "top," "bottom," "side," "short," "long," "up," "down," and "below" used herein are merely for ease of description and refer to the orientation of the components as shown in the figures. It should be understood that any orientation of the garments 10, 30, 40 or 50, and the components thereof described herein is within the scope of the present invention.

Referring now to the drawings, wherein the showings are for purposes of illustrating the present invention and not for purposes of limiting the same, FIGS. 1-5 show the outside of a first embodiment of a posture improvement garment 10, which is configured to be worn by a user 12 and which is configured to envelop at least a portion of the user's lumbo-pelvic region, hips and at least a portion of the legs or lower extremities, collectively known as the core. In this regard, the garment 10 is generally configured to be similar to one of a pair of shorts or pants (e.g., a pair of compression shorts or pants). While the illustrated garment 10 is designed as a "pull-up" style, the garment may also be provided with an open or partially open front, back or side portion, which is selectively closeable by means of known garment closure systems, such as a zipper, buttons, snaps, and the like. The garment 10 includes a main body portion 13 that has a front 13a, back 13b, right side 13c and left side 13d and first and second leg portions 14 that each define an axis. In the appropriate embodiments of the different garments 10, 30, 40 and 50 described below, the first and second leg portion 14 each include an upper leg portion 14a (garments 10, 30, 40 and 50), lower leg portion 14b (garments 30, 40 and 50), knee portion 14c (garments 30, 40 and 50) and shin portion 14d (garments 40 and 50).

Proprioceptive effects are achieved by the use of a strap system 100 that includes strategically placed straps 16, stretch panels 18 and grip layers 20, integrated directly into or sewn together, or sewn directly into the material used to fabricate the garment 10. It will be understood that the grip layer 20 is essentially a layer or patch for cuing or stimulating the nerve receptors responsible for proprioceptive feedforward and feedback. As a result, the garment of the present invention is particularly suited for the consumer market, as they are attractive and comfortable. It will be understood that the strap system 100 can include straps that are adjustable and are affixed by the user, as shown in the figures or the strap system can include straps that are integral with the garment (are not adjustable). In a preferred embodiment, the strap system 100 twists each leg in a spiral or helix manner to rotate the leg toward where the muscles are underused and weak. As can be seen in the figures, the straps 16 on each of the garments 10, 30, 40 and 50 are all positioned so that they extend in a spiral about the axis of the leg portions 14. The spiral or helix may extend at any angle.

Regarding material from which the garment 10 may be fabricated, it is preferred that the material be thin, and have an elastic quality that stretches or moves with the user's body, in order to provide a desirable form-fitting feature such that pressure may be readily applied to the surface of the user's skin in order to enhance neuromuscular stimulation thereto. The material may contain, but not be limited to, polyester, lycra, spandex, elastic, nylon, Fabrifoam® and the like, and is preferably a combination of these materials for different portions of the garment, as described below. It may have metal ions woven into it, or other mechanical sweat wicking, temperature regulating materials which are known in the art and function in an equivalent way to regulate temperature and wick moisture. Its breathability and/or moisture wicking capabilities function to improve the user's comfort level during periodic wearing of the garment.

As shown in FIGS. 1-5, in a preferred embodiment, the strap system 100 includes a plurality of leg straps 16 and two ab straps 17 (right and left ab straps are referred to individually herein as 17a and 17b respectively). In the embodiment shown in FIGS. 1-5, the straps 16 are a single piece of material that each have an unattached front strap portion 16a an anchor portion 16b and an unattached rear strap portion 16c. However, it will be understood that the unattached front strap portion 16a and unattached rear strap portion 16c are basically independent straps that can be affixed and unaffixed to the main body portion 13 as desired. The remainder of the garment is comprised of a series of panels 18, that are preferably made of a four-way elastic material. However, these panels do not have to be elastic.

Figure 5:
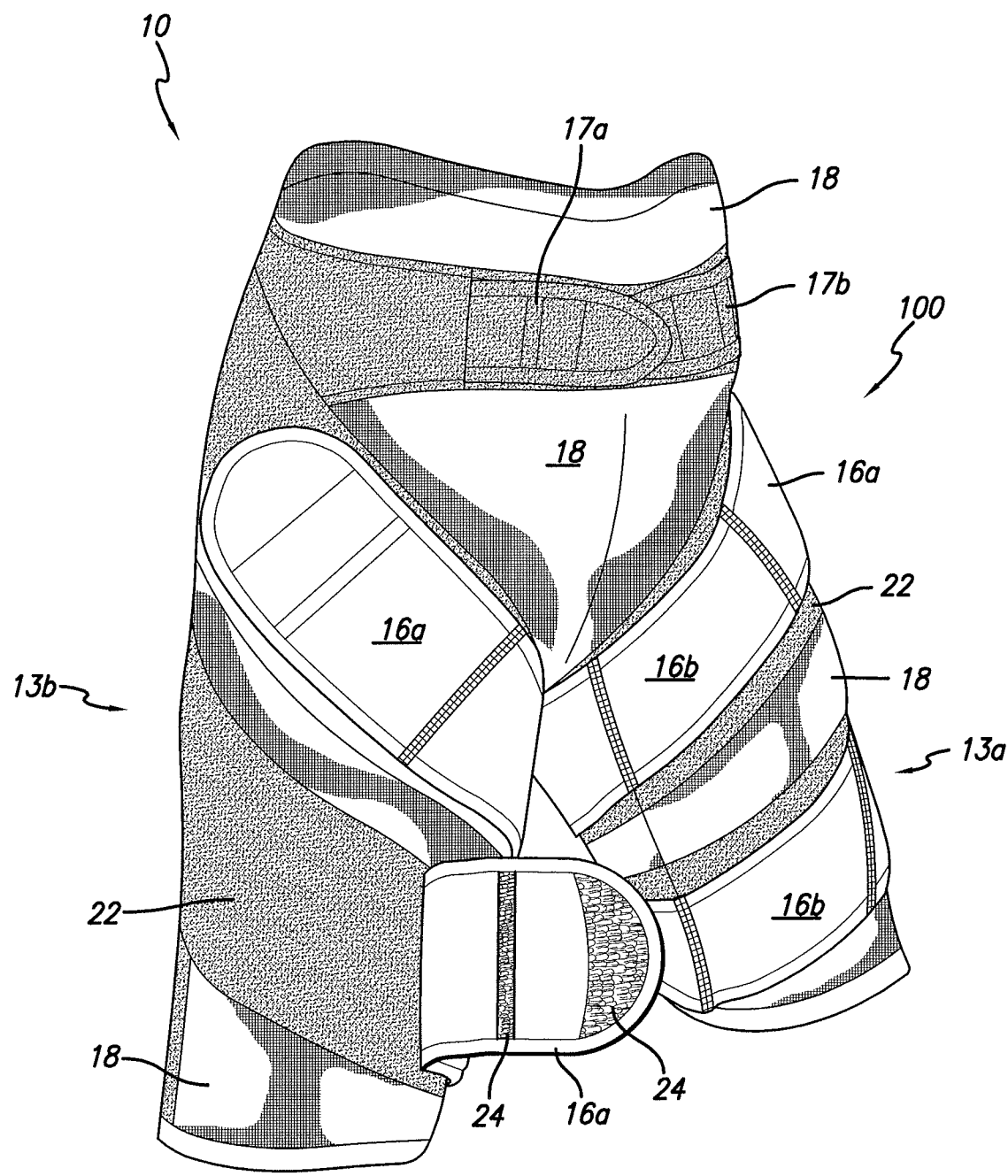
FIG. 5 is a perspective view of the garment of FIG. 1, showing another one of the straps unaffixed.
Figure 6:
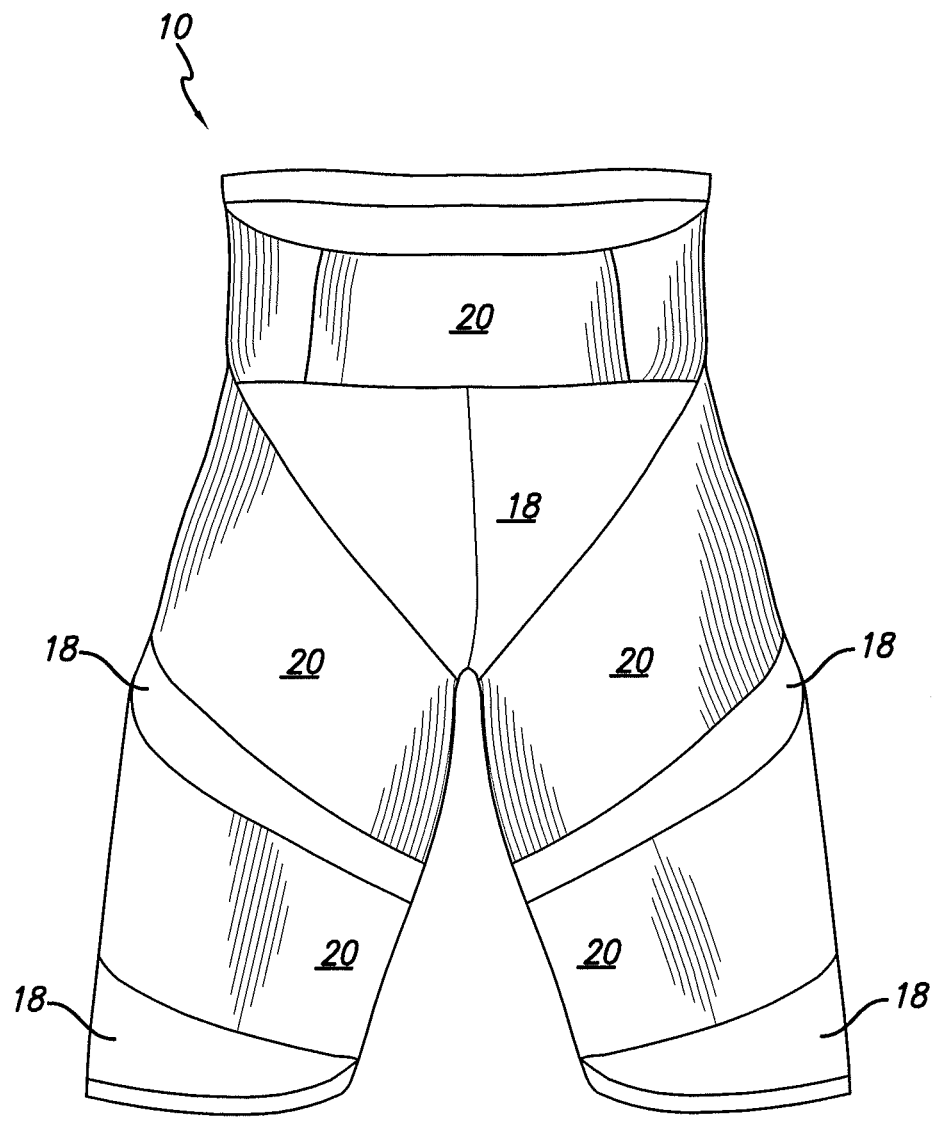
FIG. 6 is a front elevational view of the garment of FIG. 1 inside out and showing the grip layers on the inside thereof.
Figure 7:
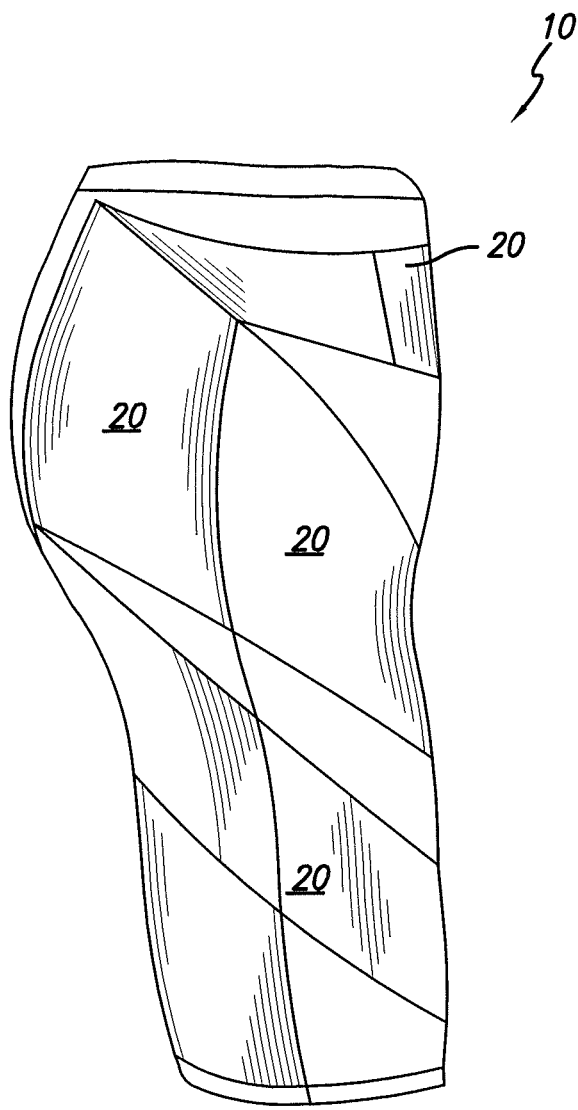
FIG. 7 is a right side elevational view of the garment of FIG. 1 inside out and showing the grip layers on the inside thereof.
Figure 8:
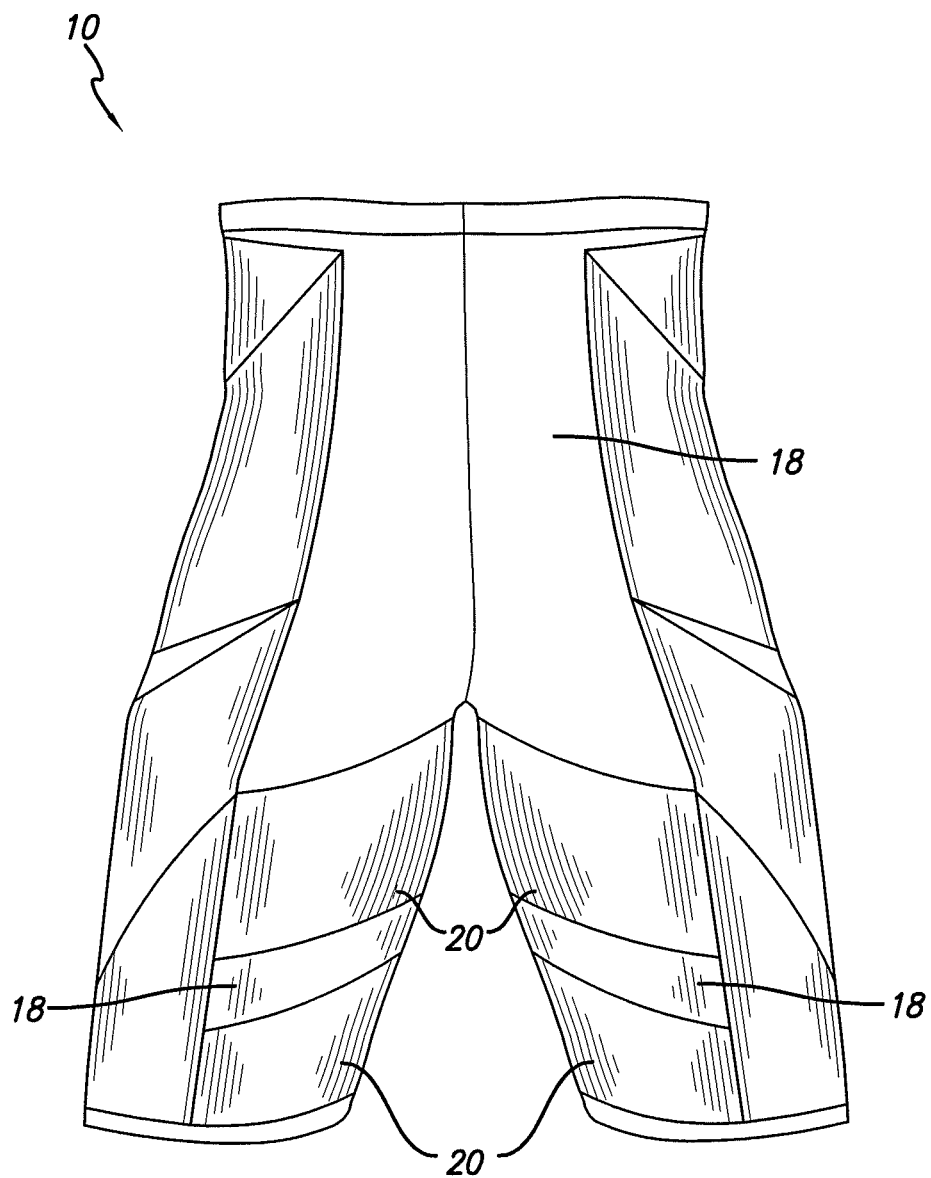
FIG. 8 is a rear elevational view of the garment of FIG. 1 inside out and showing the grip layers on the inside thereof.

FIGS. 6-8 show the garment 10 inside-out to illustrate the preferred arrangement or pattern of the base grip layers 20. The base grip layers 20 are positioned underneath the straps 16 and 17. This can be seen by comparing, for example, FIG. 2 to FIG. 6 to see that the base grips layers 20 have the same configuration as the straps 16 and 17. Therefore, the straps 16 and 17 overly a grip layer 20. As shown in FIGS. 6-8 other baser grip layers 20 can be positioned at locations where they will not be underneath a strap (for example, see the side leg and butt areas in FIG. 7). This may be for proprioceptive reasons or may be to help prevent migration of the garment or for ease of manufacture. When the garment 10 is worn by a user 12, the base grip layer 20 is in contact with the skin. The base grip layer 20 is preferably made of a material that is tacky or provides grip on the skin for providing the desired proprioceptive effects. In another embodiment, the entire layer that is in contact with the skin can be a grip layer (i.e., made of Fabrifoam® or the like).

Figure 9:
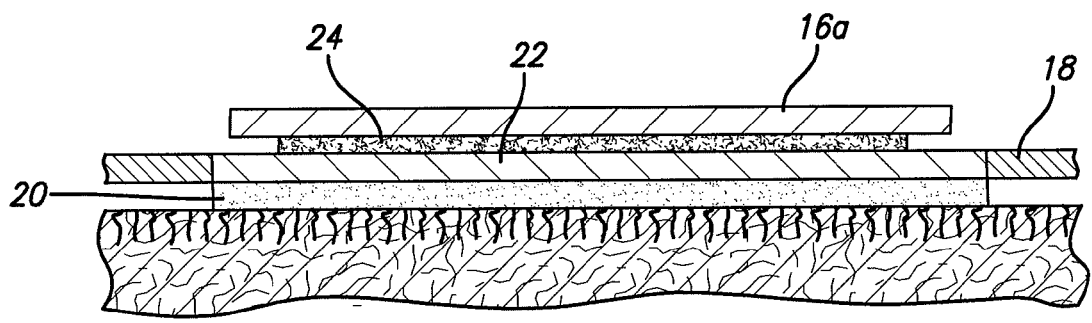
FIG. 9 is a cross-section taken along line 9-9 of FIG. 4, showing the front strap portion over the connector layer, the base grip layer and the user's skin.

Referring once again to FIGS. 1-5, in a preferred embodiment, at least the unattached front and rear strap portions 16a and 16c of the leg straps 16 is positioned over a hook and loop or connector layer 22. Each of the front and rear strap portions 16a and 16c has at least one and preferably two hook and loop tabs or connectors 24 that allow the user to affix the straps portions 16a and 16c to the connector layer 22 and to adjust how much tension (or sensorimotor stimulation) on the muscle is comfortable, the specific direction of compression, and support, as described more fully below. It will be understood that any type of connection between the front and rear strap portions 16a and 16c of the straps 16 and the connector layer 22 is within the scope of the present invention. For example, snaps, buttons, adhesive, hooks or the like are also within the scope of the present invention. In another embodiment, the connector layer 22 can be omitted and the unaffixed strap portions 16a and 16c can be connected directly to the base grip layer 20. As will be described more fully below, what is important is that the strap 16 overlies and places tension on the base grip layer 20 (which is in contact with the skin), which cues responses in the nerve receptors in the skin. FIG. 9 shows a cross section through the garment 10 at line 9-9 of FIG. 4. FIG. 9 shows the various layers of the garment 10 and, in particular, the grip layer 20 in contact with the skin and the nerve receptors therein.

Figure 4:
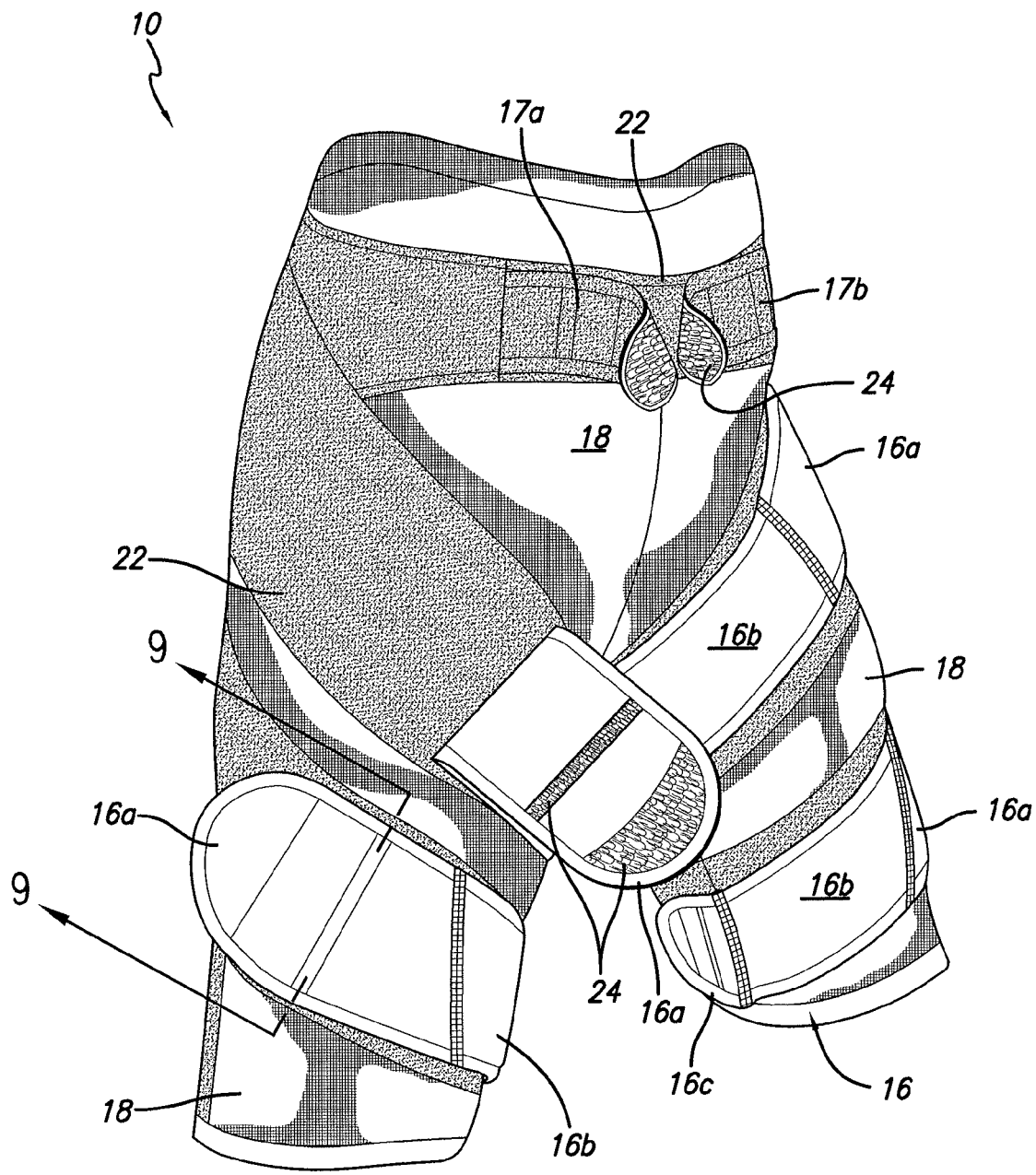
FIG. 4 is a perspective view of the garment of FIG. 1, showing one of the straps unaffixed.

In a preferred embodiment, the straps 16 and 17 are fabricated of a two-way elastic material, e.g., FABRIFOAM® or the like and, as discussed above, each of the front and rear portions 16a and 16c include two hook and loop or connector tabs 24 (which provides a double anchor system). However, this is not a limitation on the present invention. In a preferred embodiment, the anchor section 16b of the leg straps 16 is sewn (stitching is marked 16d—e.g., see the lower left strap in FIG. 2) or otherwise permanently attached to the layer underneath. FIGS. 4 and 5 illustrate one of the front strap portions 16a when it is not attached to the connector layer 22.

In use, after a user puts the garment 10 on, for each of the leg straps 16, the user pulls the unaffixed front strap portion 16a and connects the first hook and loop tab 24 to the connector layer 22 and then pulls the remainder of the unaffixed front strap portion 16a and connects the second hook and loop tab 24 to the connector layer 22. This is then repeated for each of the rear strap portions 16b. In a preferred embodiment, the back leg strap portions 16c are anchored first. However, this is not a limitation on the present invention.

It will be understood by those skilled in the art that the muscles in the outside of a human's leg generally become dominant, short and tight from overuse and understretch and the body tends to rotate toward tension, thereby causing external rotation of the hip, lower leg and foot, increasing pronation, and serial distortion. All of these imbalances in the muscles that cause this motion collectively create what is known as lower crossed syndrome. For instance, this increased pronation and valgus stress on the knees causes increased stress on joint surfaces and neuromuscular structures including mechanoreceptors and nociceptors within the joint and surrounding soft tissues. The present invention helps derotate the lower extremities and return to a more optimal anatomically neutral and functionally balanced position. When the leg straps 16 are connected as described above (as shown in FIG. 2), the anchor portion 16b or 16d creates a base or anchor, and the two-way stretch causes the leg to rotate or return to the inner leg, where the muscles are underused and weak. This is illustrated by the arrows on straps 16 in FIGS. 2, 3 and 10. The arrows show that the front and rear strap portions 16a and 16c (generally, straps 16) have a directional influence on the body of the user 12. It forces the user to use underused muscles while the overused muscles are held in a position that causes them to stretch, relax and unload the joints of the hip, lower back, knee, etc. This is what unloads the pressure and stress from the joints and places it back into a more physiologically capable balance of human muscle and joint function. The overtoned/overused muscles include, for example, the gluteus medius, the vastus lateralus, tensor fascia lata, psoas, illicus, piriformis. The undertoned/underused muscles include, for example, gracilas, pecitinious, adductor brevis, adductor longus and vmo.

It will be understood by those skilled in the art that the strapping system 100 is based upon the concept of a concentration gradient, meaning that the straps 16 always pull back toward the larger anchor portion 16b, which is the greater mass of like material, or the seem 16d, which anchors the straps 16 to the main body portion 13. In other words, in the embodiment shown in FIGS. 1-5, the anchor portion 16b includes a greater amount of like material than does either the front strap portion 16a or the rear strap portion 16c. It is not a limitation that the anchor portion 16b include more material (as is the case when the anchor is simply a seem 16d or the like). However, the concentration gradient is more effective if it does. The concept works best when there is more anchored material than loose material and when the materials are the same and include a two-way stretch.

Figure 2:
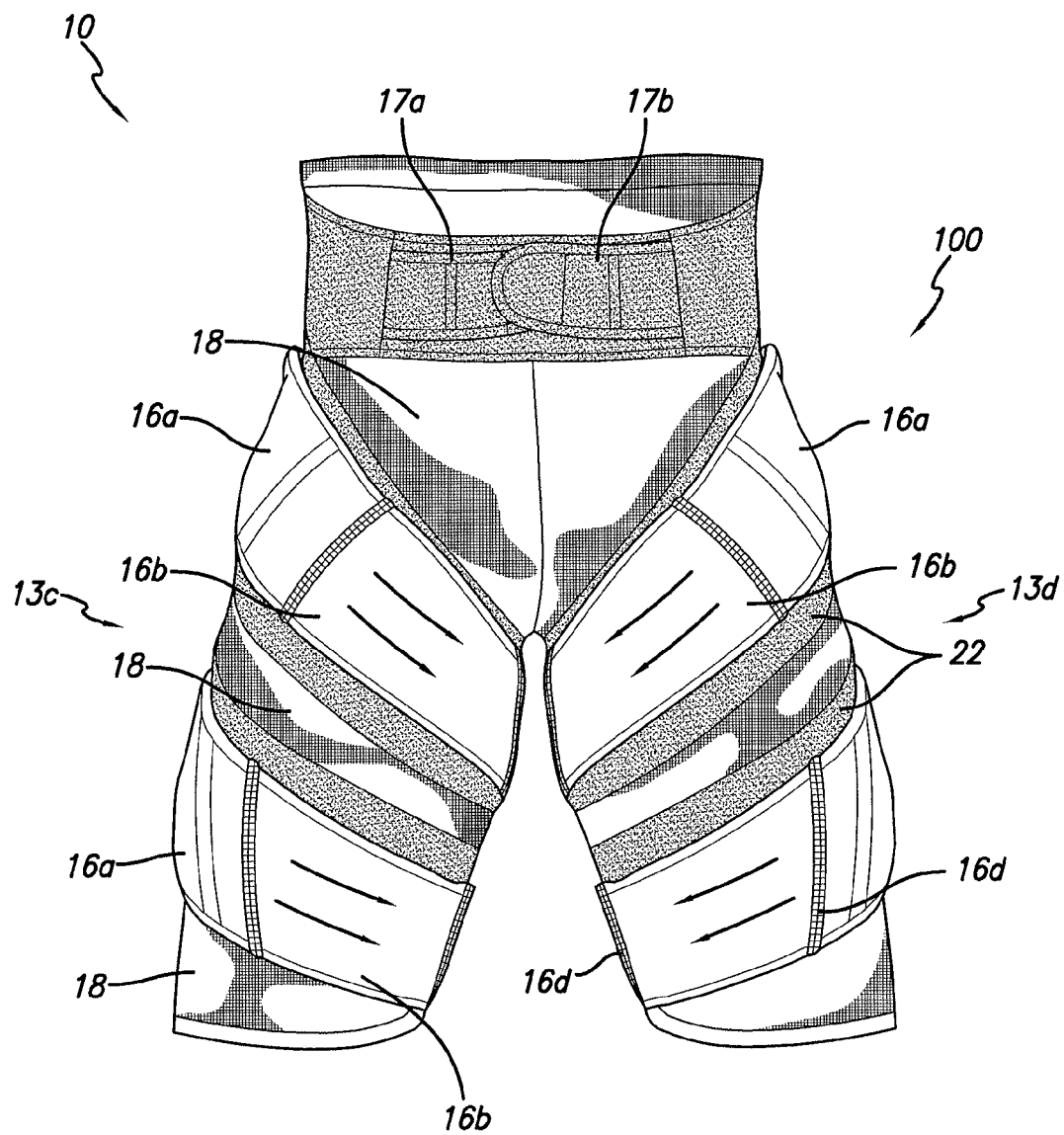
FIG. 2 is a front elevational view of the garment of FIG. 1.
Figure 3:
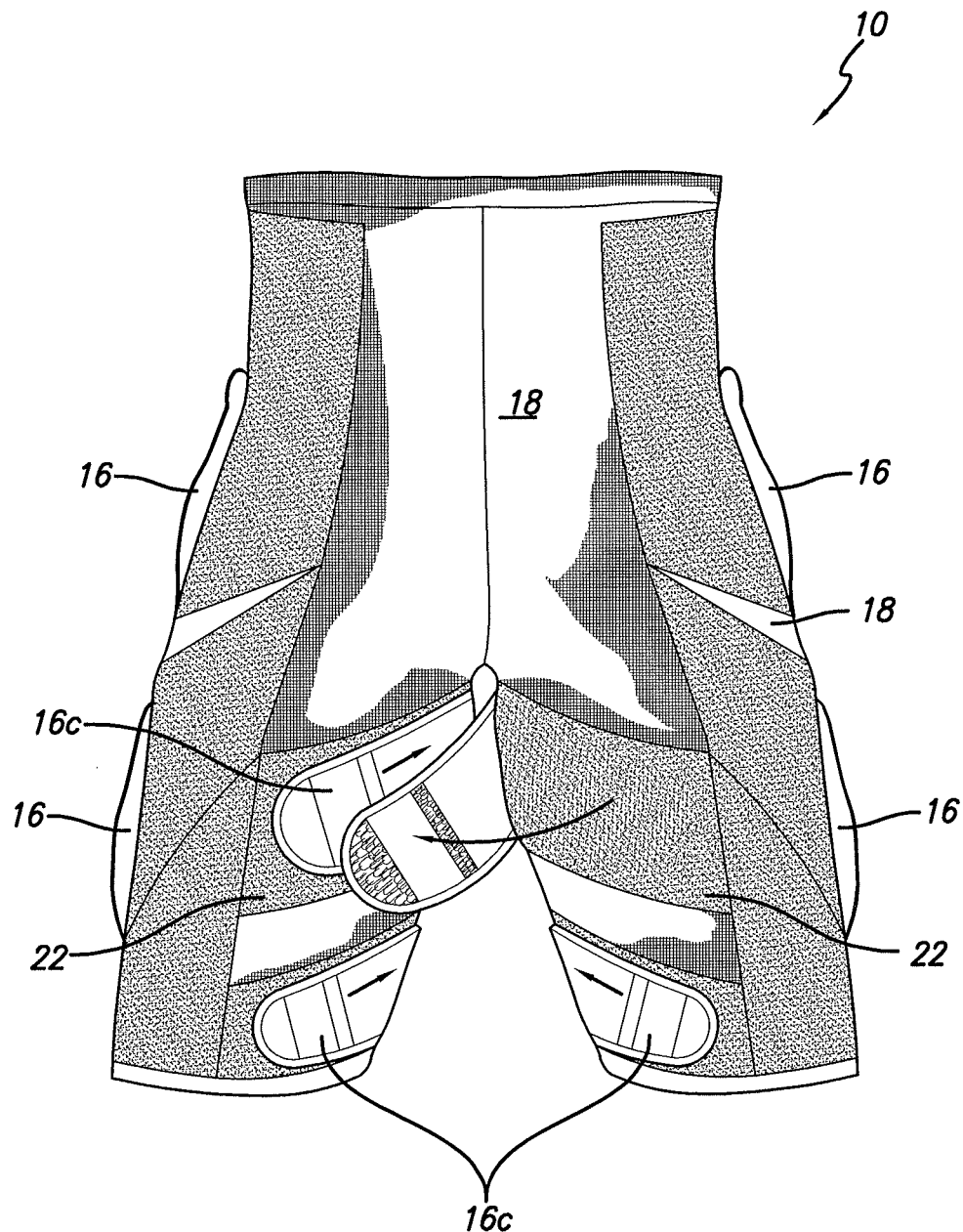
FIG. 3 is a rear elevational view of the garment of FIG. 1.

The ab straps 16 also work via a concentration gradient. As is shown in FIGS. 4-5, for a right handed user, the left ab strap 17b is placed underneath lightly and the right ab strap 17a is positioned thereover with more pull. This helps de-rotate the right hip back into a neutral anatomical position and helps prevent predictable antiversion of, for example, the right hip on right handed person. As is shown in FIGS. 1-2, for a left handed user, the right ab strap 17a is placed underneath lightly and the left ab strap 17b is positioned thereover with more pull. This helps de-rotate the left hip back into a neutral anatomical position. One of skill in the art will understand that the top strap cues the lower abs to fire and de-rotates the pelvis and shuts off or relaxes the overtoned/inhibited hip flexors. In order to achieve this, in a preferred embodiment, the right and left ab straps 17a and 17b include hook and loop tabs or connectors 24 on both the top and bottom thereof.

It will be understood that the strap system 100 can be modified in other embodiments of the garment. Although four leg straps 16 and one ab strap 17 (and corresponding base grip layers 20) are shown in the embodiment of FIGS. 1-9, any number of such straps 16 and 17 and of various shapes and sizes, may be employed if desired. For example, the strap system 100 may include more or less than four straps or the straps may only include unaffixed front strap portions, unaffixed rear strap portions or a combination of both. In another embodiment, the straps can be a four-way elastic or a non-elastic material, and/or can include only a single connector tab 24. It will be understood that any embodiment that includes a base grip layer against the skin and a strap positioned thereover is within the scope of the present invention. For example, an embodiment can include a pair of form fitting shorts that include a base grip layer inside that contacts the skin and straps on the outside. The straps 16 and 17, together with the base grip layers 20 function to stimulate muscles that are too tight (the straps/grip layers will stretch these muscles), or too loose and undertoned (the straps/grip layers will add tone to these muscles and encourage/stimulate them to work).

Figure 10:
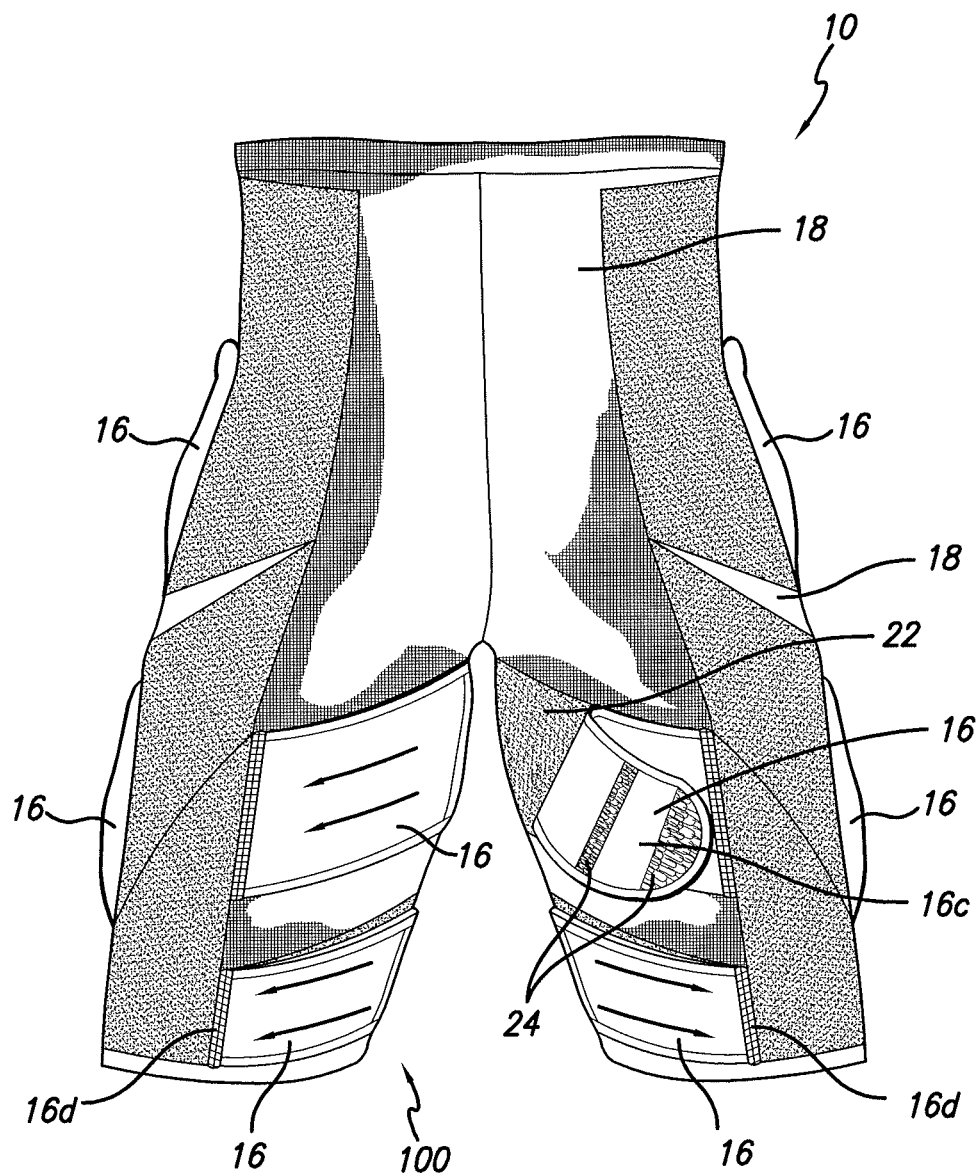
FIG. 10 is a rear elevational view of the garment of FIG. 1 with the rear straps in a different position in accordance with a preferred embodiment of the present invention.

It will be understood that different embodiments or versions of the shorts can be provided for different users and for different conditions to be corrected. The embodiment shown in FIGS. 1-5 has the rear strap portions 16c extending from the groin toward the back of the leg or hamstring. FIG. 10 shows another preferred embodiment of the garment 10, where the rear straps 16c are anchored on the rear of the leg portions 14 and extend from the rear of the leg portion 14 (adjacent the hamstring) and toward the groin. It will be understood that the grip layer pattern for this version of the garment can be similar to that shown in FIG. 6-8.

Figure 11:
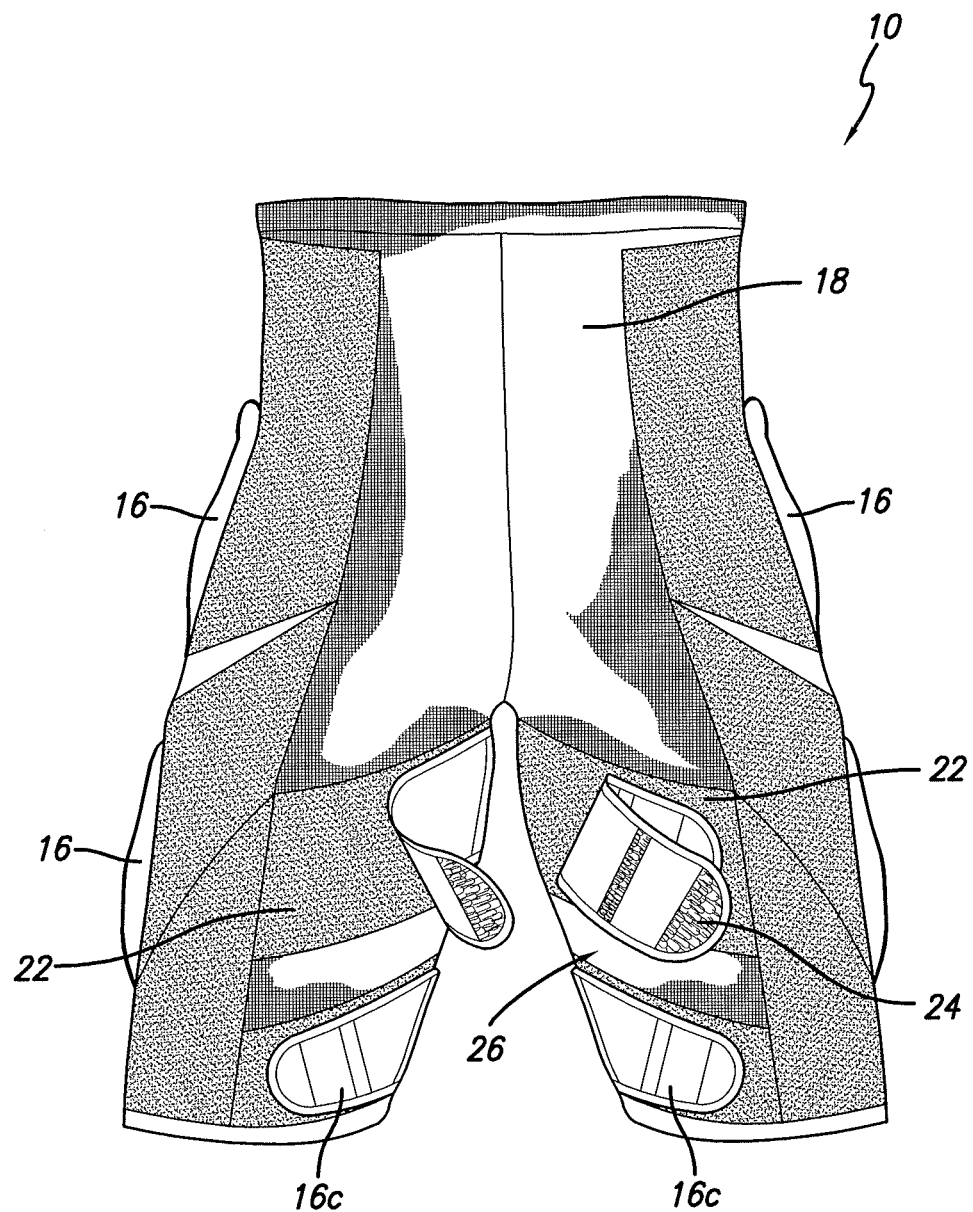
FIG. 11 is a rear elevational view of the garment of FIG. 1 with one removable strap in accordance with a preferred embodiment of the present invention.
Figure 12:
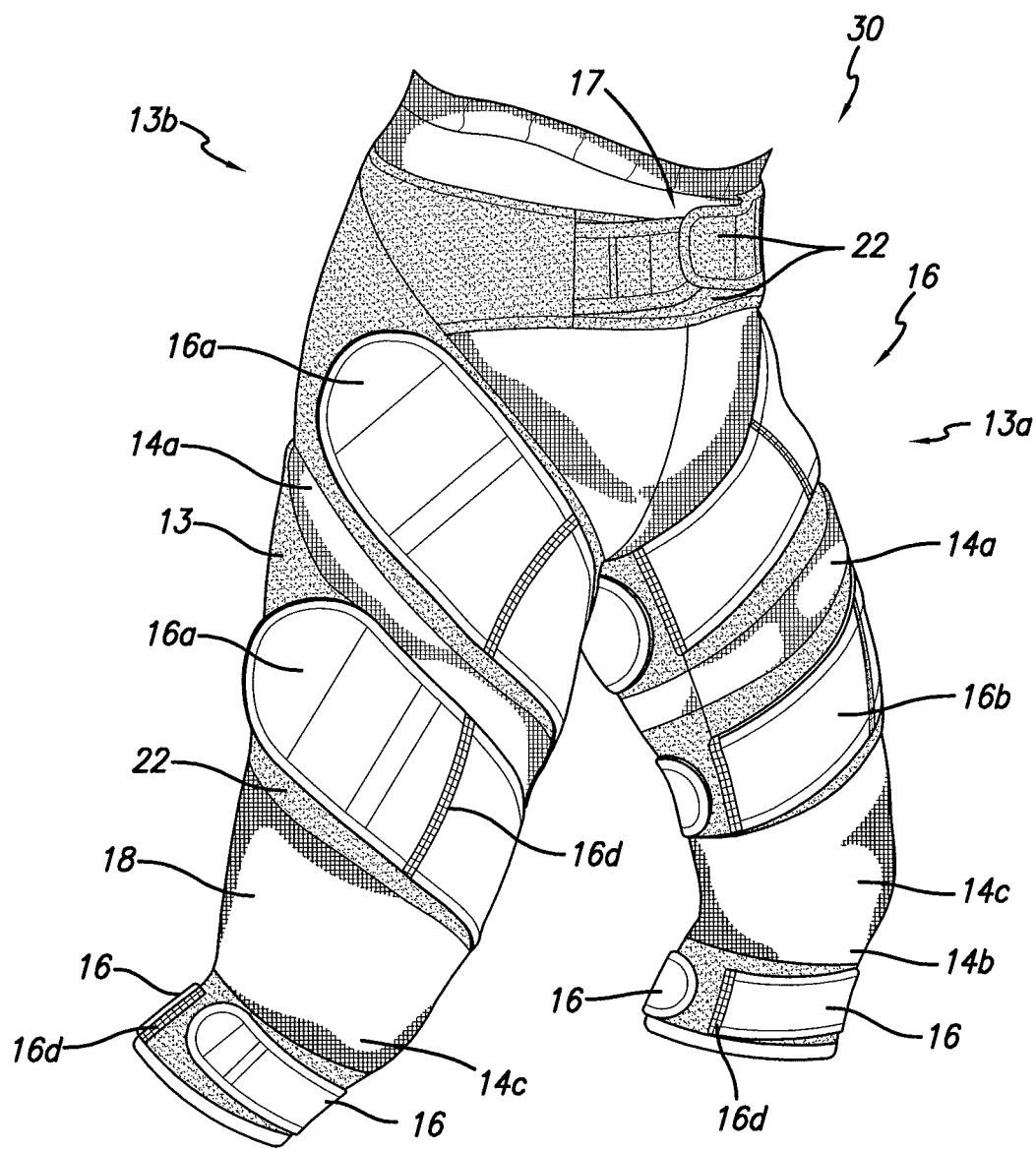
FIG. 12 is a perspective view of a garment (three quarter length pants) in accordance with another preferred embodiment of the present invention.
Figure 13:
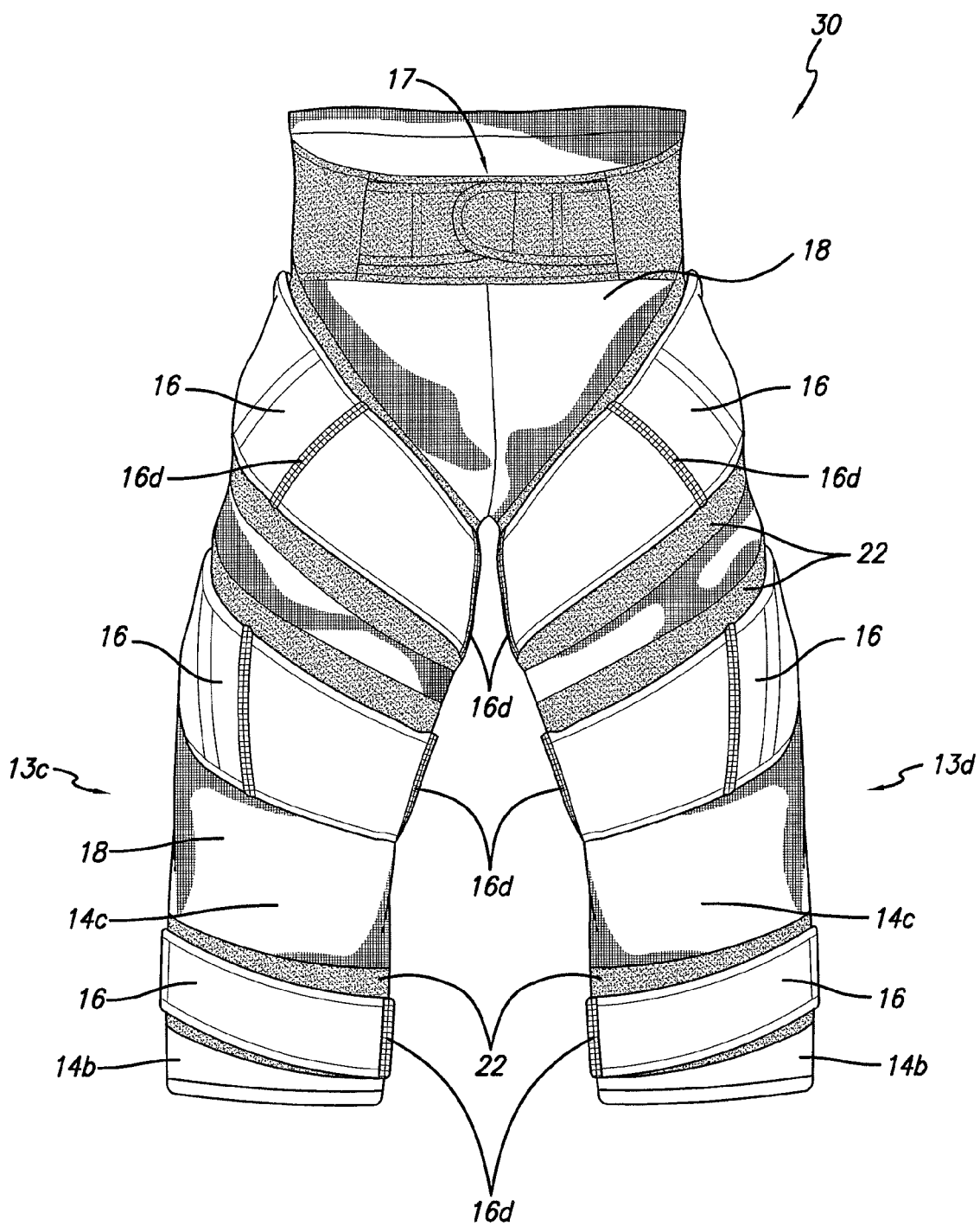
FIG. 13 is a front elevational view of the garment of FIG. 12.

FIG. 11 shows a garment 10 similar to that shown in FIGS. 1-5, except that it includes one removable strap 26. In FIG. 11, the removable strap 26 has one end unattached and the other end attached. The removable strap 26 includes hook and loop tabs or connectors 24 on both ends thereof and can include connectors 24 anywhere along its length to keep the strap 26 attached to the garment 10 as desired. The removable strap(s) 26 provide greater adjustability than straps that are permanently anchored to the garment 10.

FIGS. 12-16 show another preferred embodiment of a garment 30. In this embodiment of the present invention the garment 30 is a three quarter length pair of pants that extend just below a wearer's knee. It will be understood that the portion of the garment 30 above the knees is the same as the garment 10 described above. Therefore, only the portion of the garment 30 that is different will be described.

Figure 14:
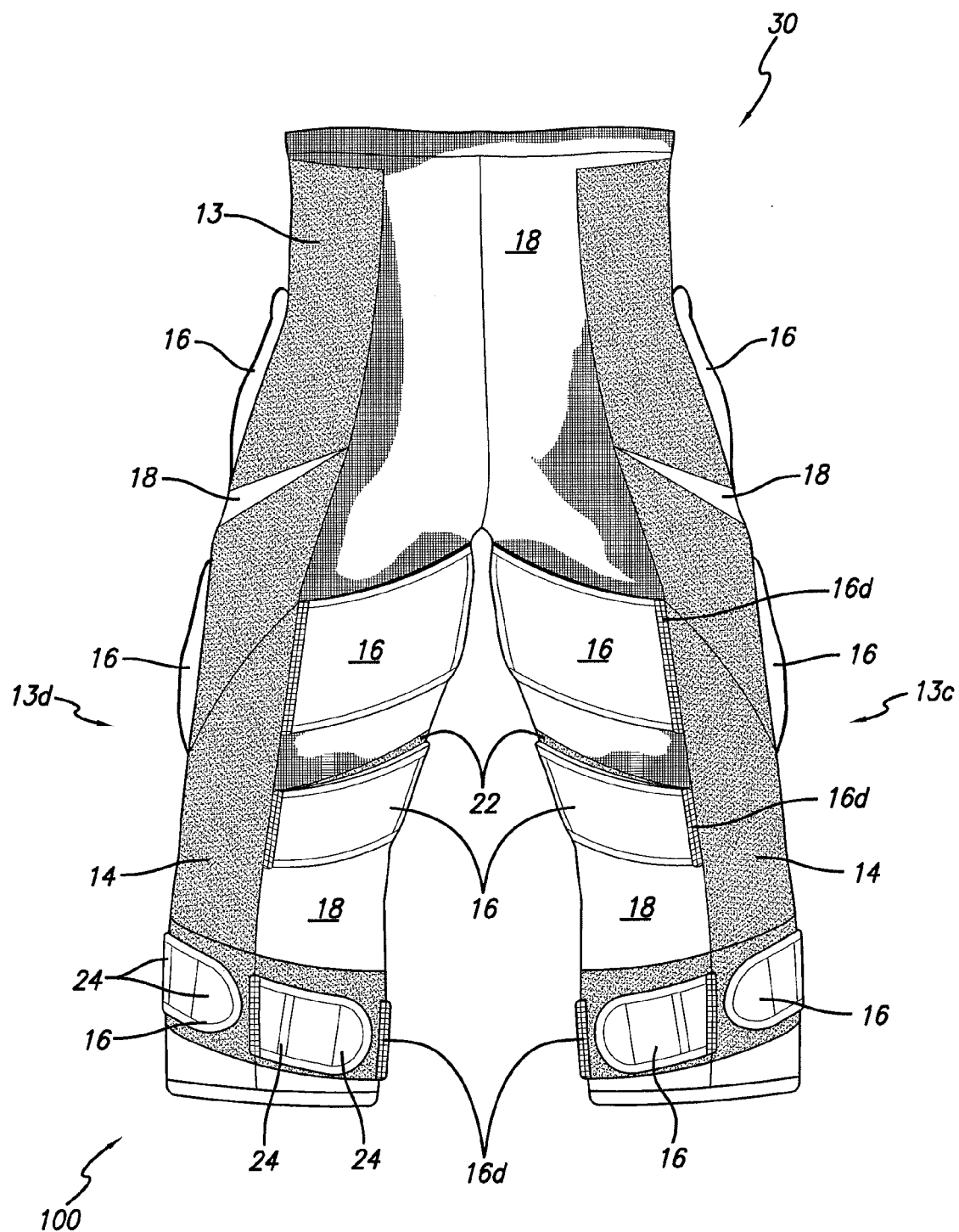
FIG. 14 is a rear elevational view of the garment of FIG. 12.
Figure 15:
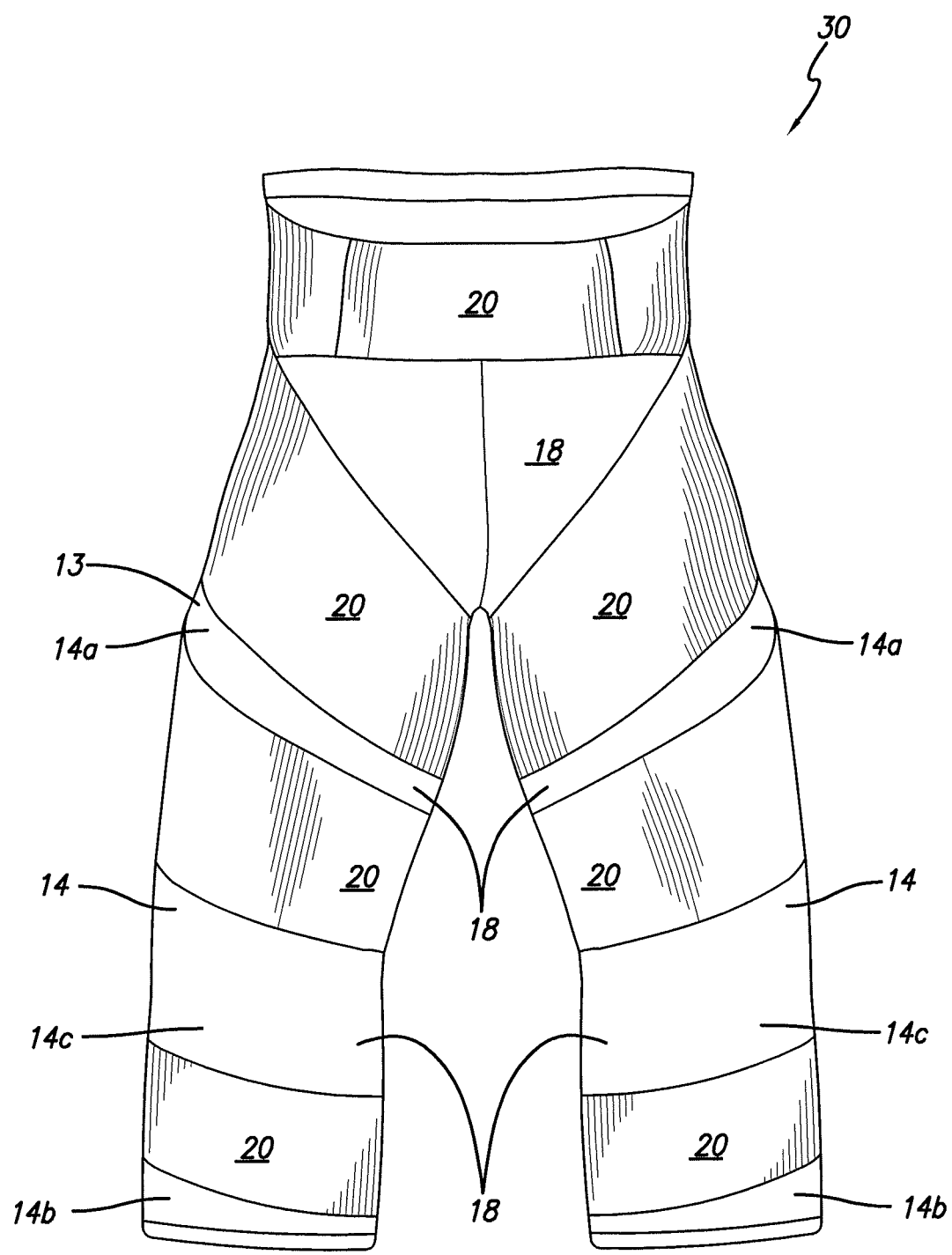
FIG. 15 is a front elevational view of the garment of FIG. 12 inside out and showing the grip layers on the inside thereof.
Figure 16:
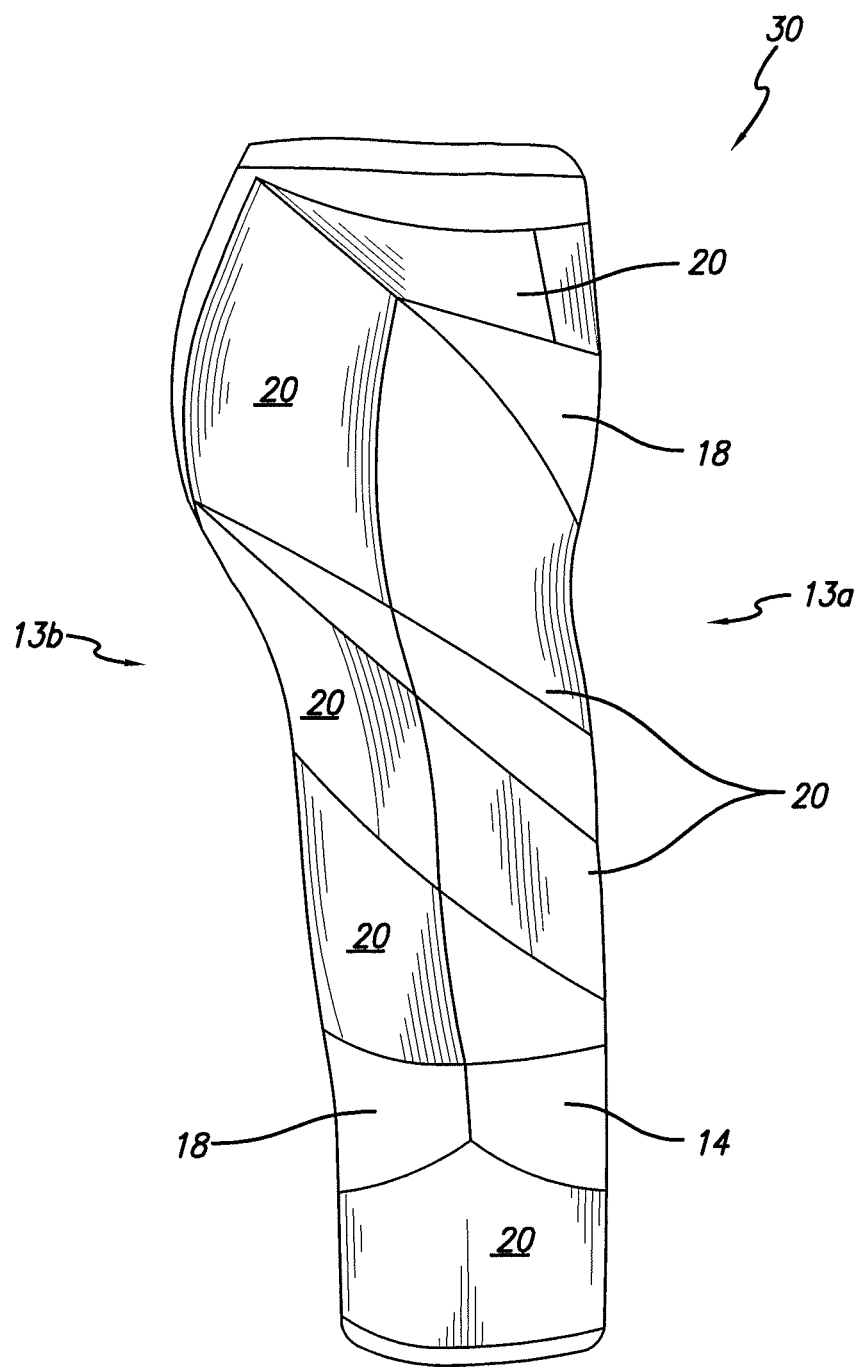
FIG. 16 is a right side elevational view of the garment of FIG. 12 inside out and showing the grip layers on the inside thereof.

Just below the knee, the garment 30 includes at least one sub-patella strap 16. In the embodiment shown in FIGS. 12-14, each leg portion 14 of the garment 30 includes two sub-patella straps 16, one that extends from the midline of medial aspect of the knee joint and extends around laterally and ending at the lateral posterior aspect of the proximal head of the fibula. Generally, it extends from the inner leg around the front. The other strap 16 extends from the midline superior posterior aspect of the trisceps surae (calf muscles) and toward the inner leg. Generally, it extends from the middle of the back of the leg toward the inner leg. As shown, the sub-patella strap 16 on the back of the leg is preferably positioned about an inch below the joint line. As can be seen in FIG. 14, the sub-patella straps extend at an angle and in a spiral direction about the axis of the leg portion 14. FIGS. 15-16 show the garment 30 inside-out to illustrate the preferred arrangement or pattern of the base grip layers 20. It will be understood that the grip layers 20 may or may not have a spiral shape to them. In an embodiment where the spiral is important, it only matters that the corresponding straps 16 have the spiral shape and that they overly a grip layer 20. In a preferred embodiment, these straps 16 in combination with the grip layers 20 cause reciprocal inhibition by creating traction and directional compression over cutaneous neuro receptors from lateral (posterior-lateral proximal head of fibula which is an area extremely dense with sensitive nerve receptors/golgi tendon organs and where many tendons attach) to medial commonly weaker, less supportive, less coordinated and less reactive to stress) causing muscles of wearer's medial thigh and lower leg to contract, tone, balance and optimally align, adding instant and improved sensory motor support and stability to the knee and lower extremity as a whole because the muscles (dynamic support system) now function with rhythm and synchrony and unload the mechanical stress that often pre loads a joint, decreases it's range of motion and function and makes it susceptible to injury of the wear and tear and traumatic nature.

FIGS. 17-21 show another preferred embodiment of a garment 40. In this embodiment of the present invention, the garment 40 is a full length pair of pants that extend to a point just above a wearer's foot. It will be understood that the majority of the garment 40 is the same as the garment 30 described above. Therefore, only the portion of the garment 40 that is different will be described.

Figure 17:
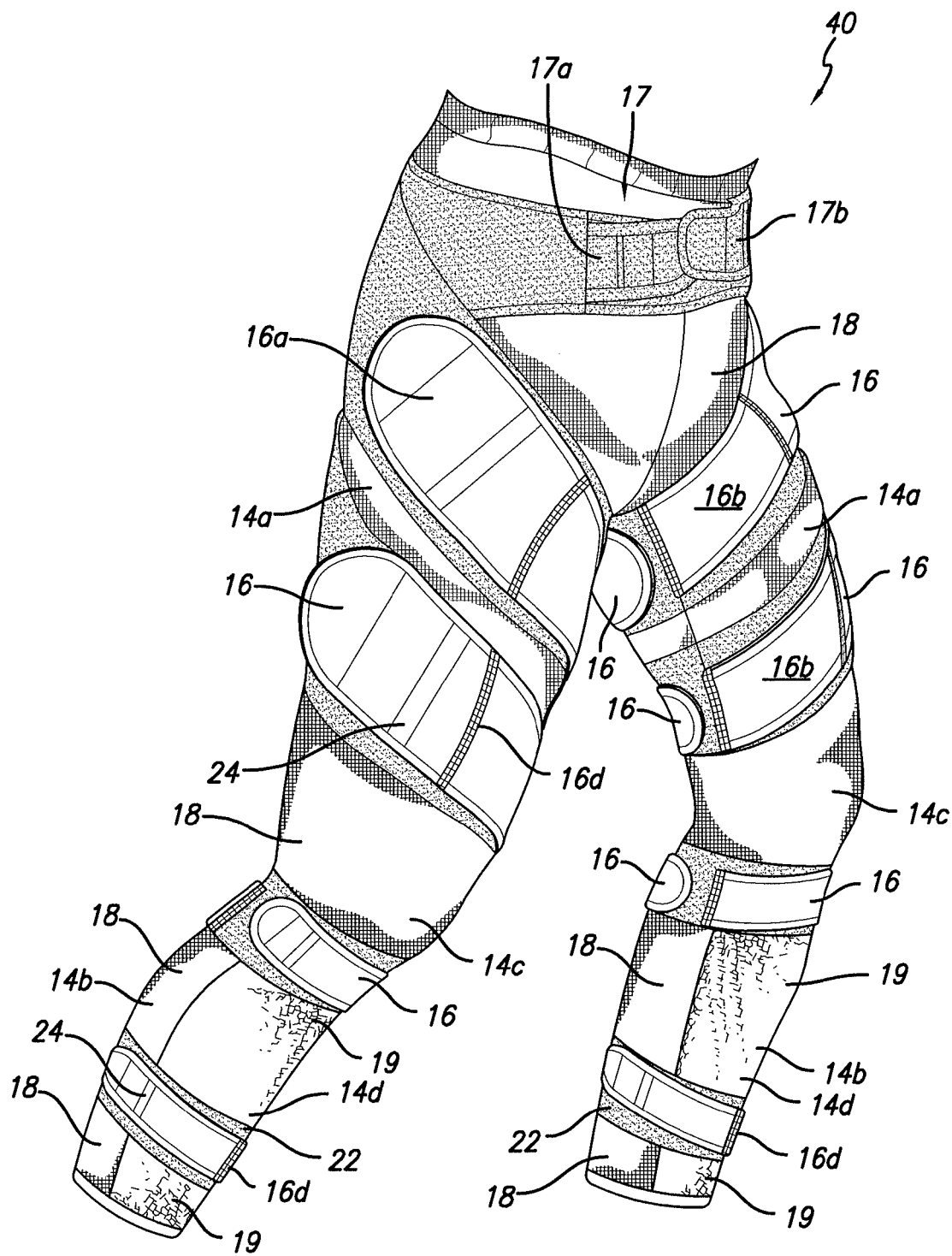
FIG. 17 is a perspective view of a garment (full length pants) in accordance with another preferred embodiment of the present invention.
Figure 18:
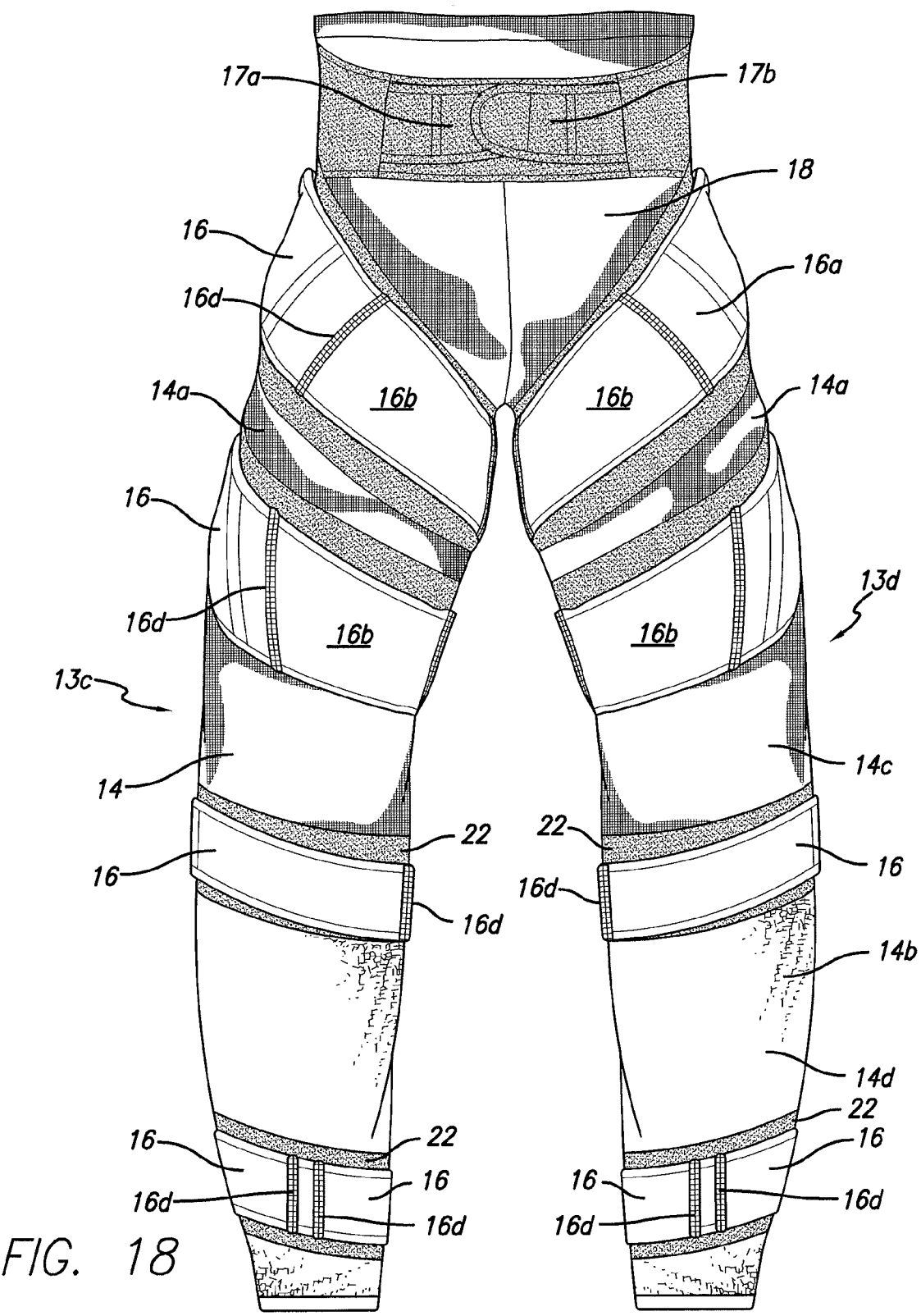
FIG. 18 is a front elevational view of the garment of FIG. 17.
Figure 19:
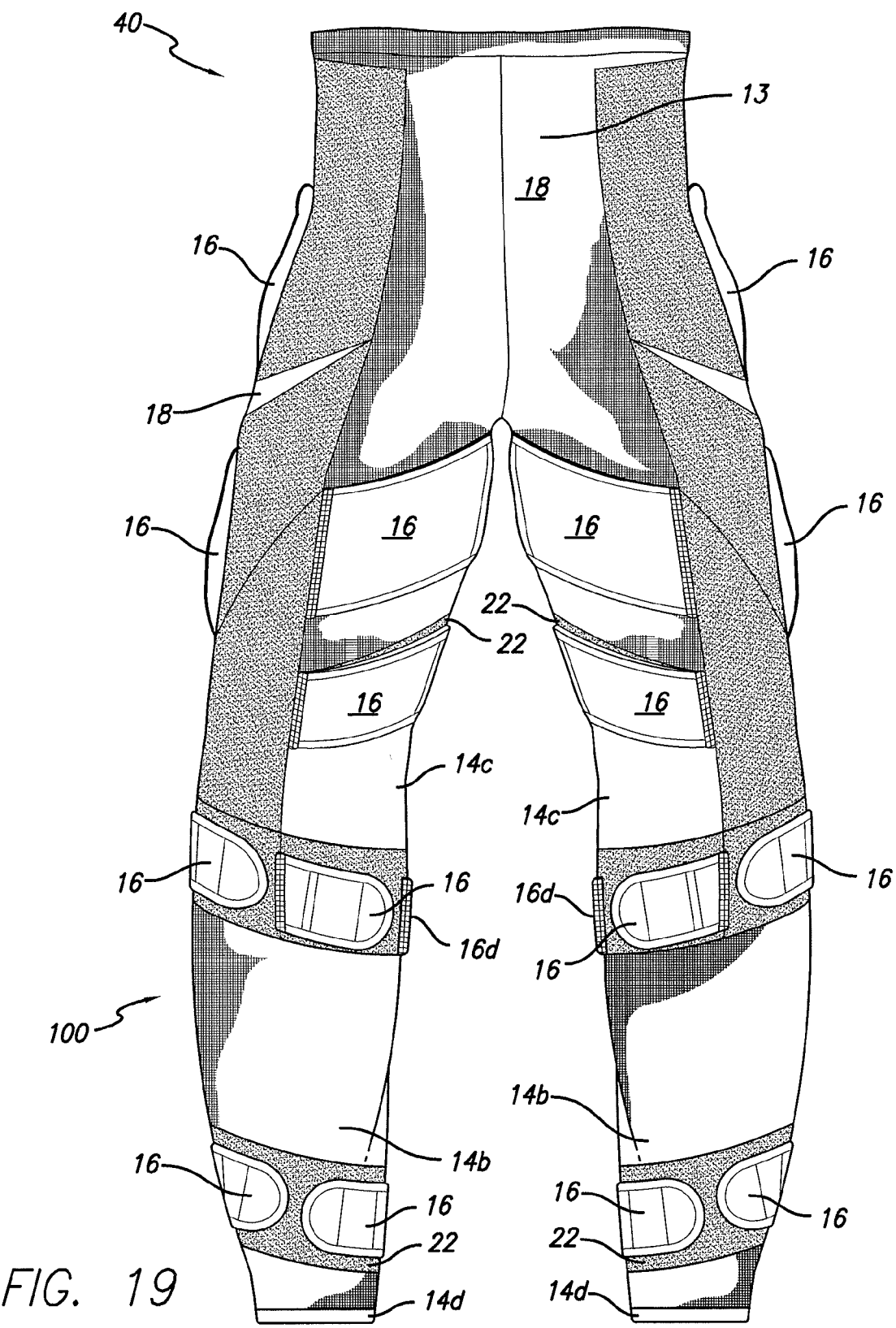
FIG. 19 is a rear elevational view of the garment of FIG. 17.
Figure 20:
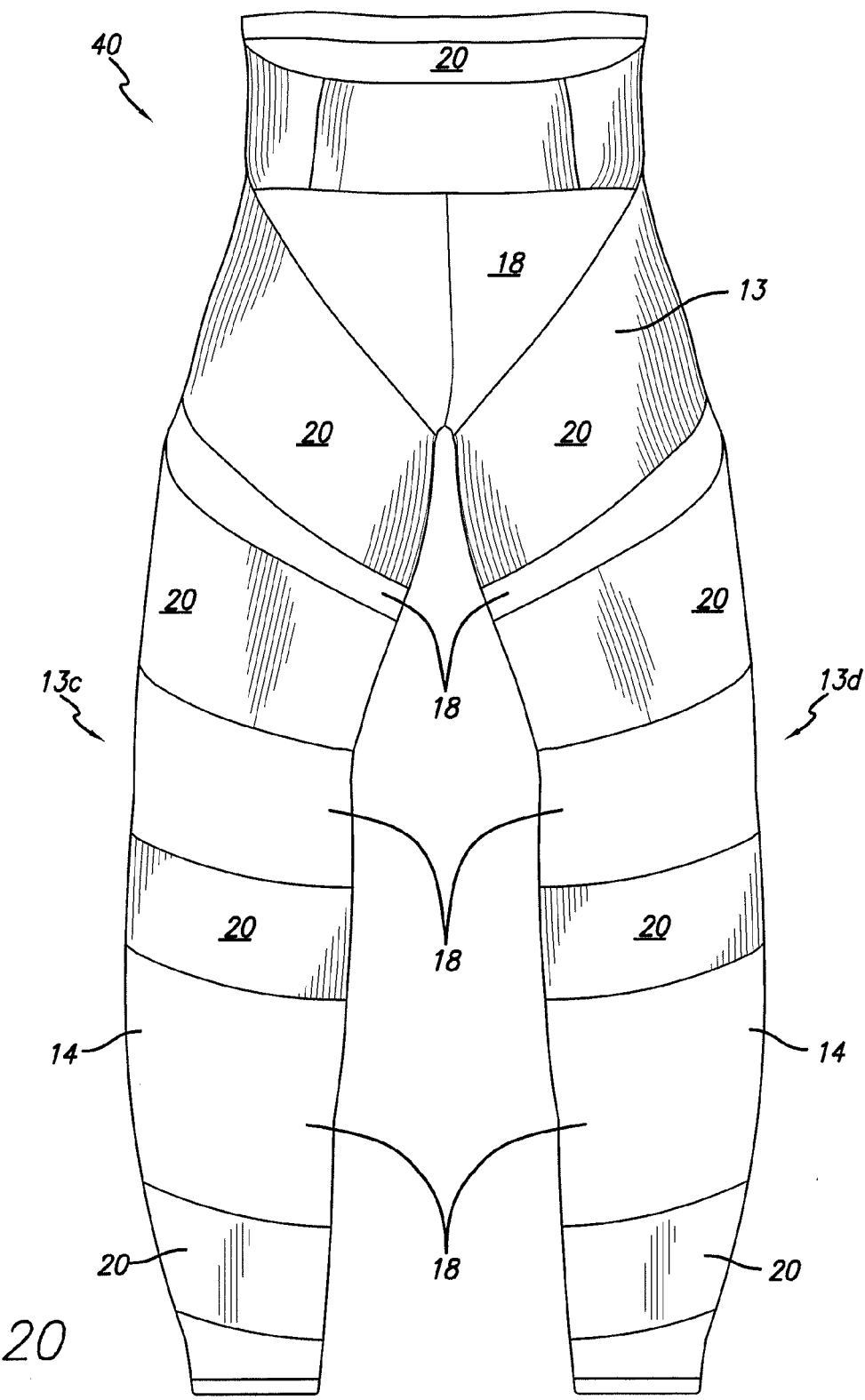
FIG. 20 is a front elevational view of the garment of FIG. 17 inside out and showing the grip layers on the inside thereof.
Figure 21:
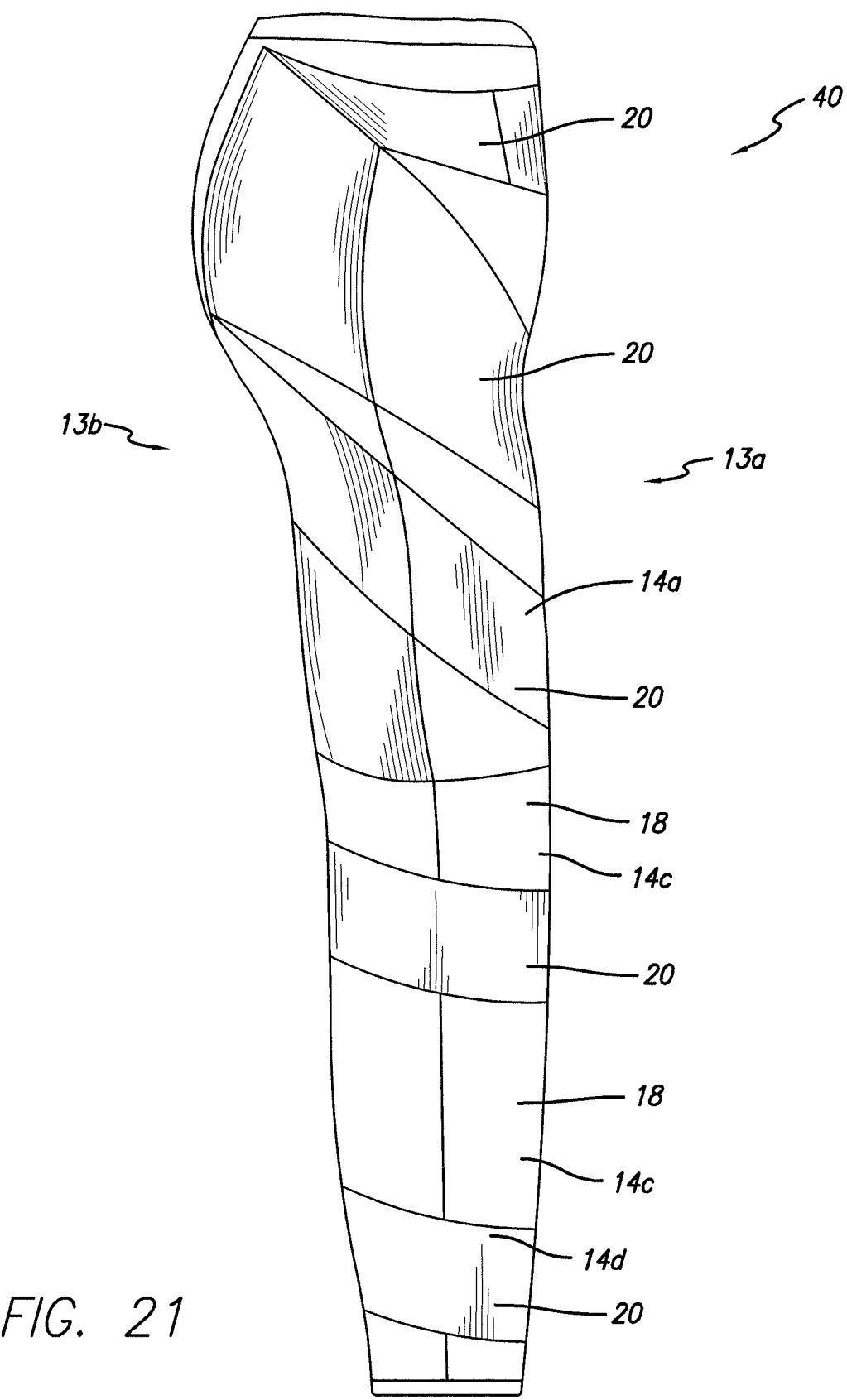
FIG. 21 is a right side elevational view of the garment of FIG. 17 inside out and showing the grip layers on the inside thereof.

In a preferred embodiment, the garment 40 includes at least one shin or tibia strap 16, and preferably a pair of shin straps 16. In the embodiment shown in FIGS. 17-19, each leg portion 14 of the garment 40 includes two shin straps 16. In a preferred embodiment, the shin straps 16 on each leg portion 14 extend from the middle of the front of the shin at the tibia and around the inside and outside of the shin, respectively, and toward the back of the leg (on both leg portions 14). However, the placement or location of the stitching 16d or anchor is not a limitation on the present invention. As can be seen in FIG. 18, the shin straps 16 extend in a spiral manner. FIGS. 20-21 show the garment 40 inside-out to illustrate the preferred arrangement or pattern of the base grip layers 20. In a preferred embodiment, these shin straps 16 in combination with the grip layers allow the wearer to adjust and control lower leg internal and external rotation (duck walk or opposite gait known as pigeon toe). Many people are either lower extremity gait pronators (90+% of the population) or a supinator. The shin strap 16 allows the wearer to help correct these problems and to adjust and control lower leg internal and external rotation as desired. This helps decrease serial distortion caused by over pronation or over supination. The tibia strap 16 helps prevent midial tibial torsion syndrome (shin splints), high ankle sprains and peroneal tendonopathy. In an embodiment of the invention, as shown in FIG. 17, between the sub-patella straps 16 and the shin straps 16, the lower leg portion 14b can include two different materials, a two-stretch material portion 19 on the front and the normal stretch panel 18 on the back. However, this is not a limitation and this entire portion of the pants can also be made of four-way stretch panel 18 or two-way stretch material 19.

Figure 23:
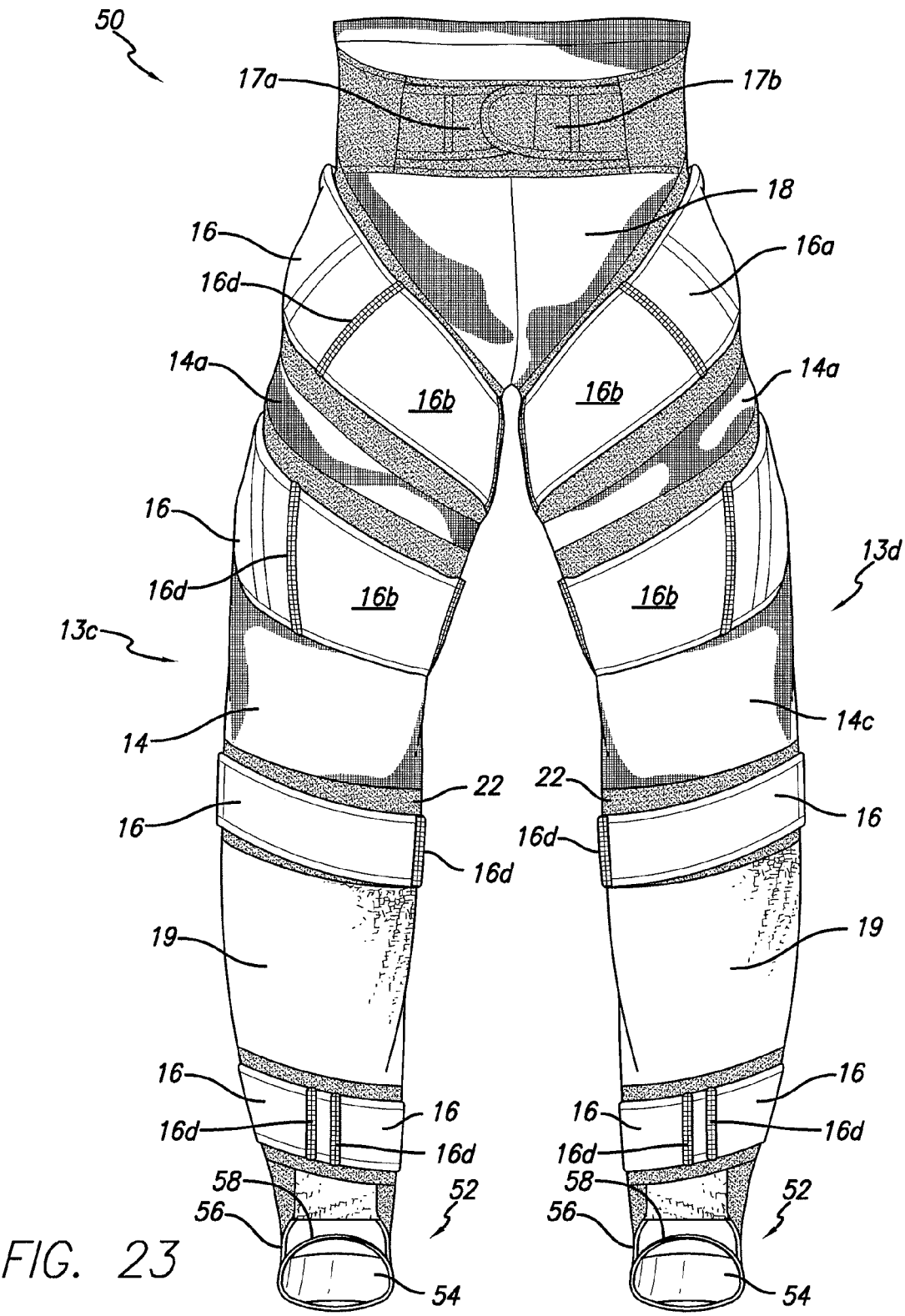
FIG. 23 is a front elevational view of the garment of FIG. 22.
Figure 24:
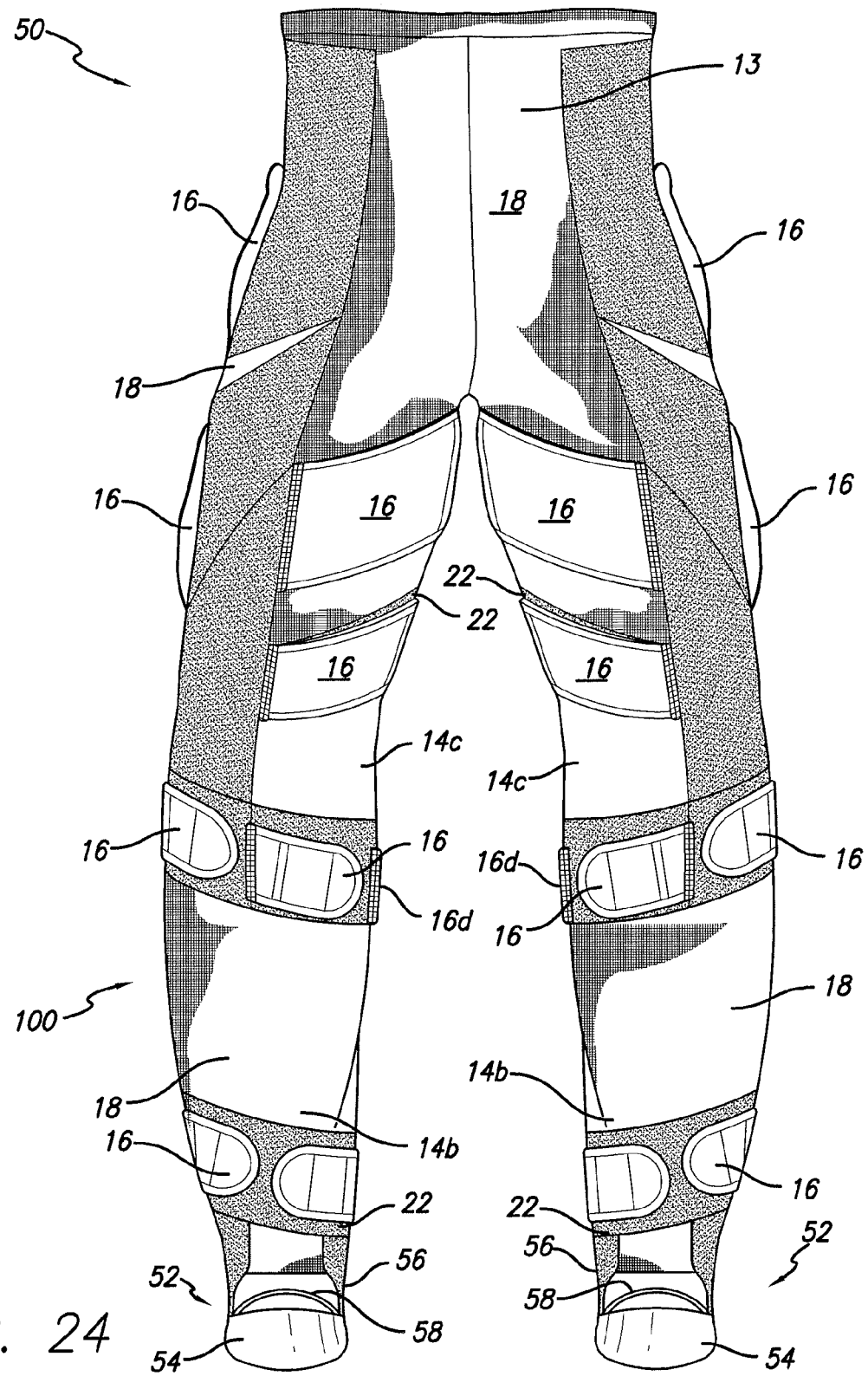
FIG. 24 is a rear elevational view of the garment of FIG. 22.
Figure 25:
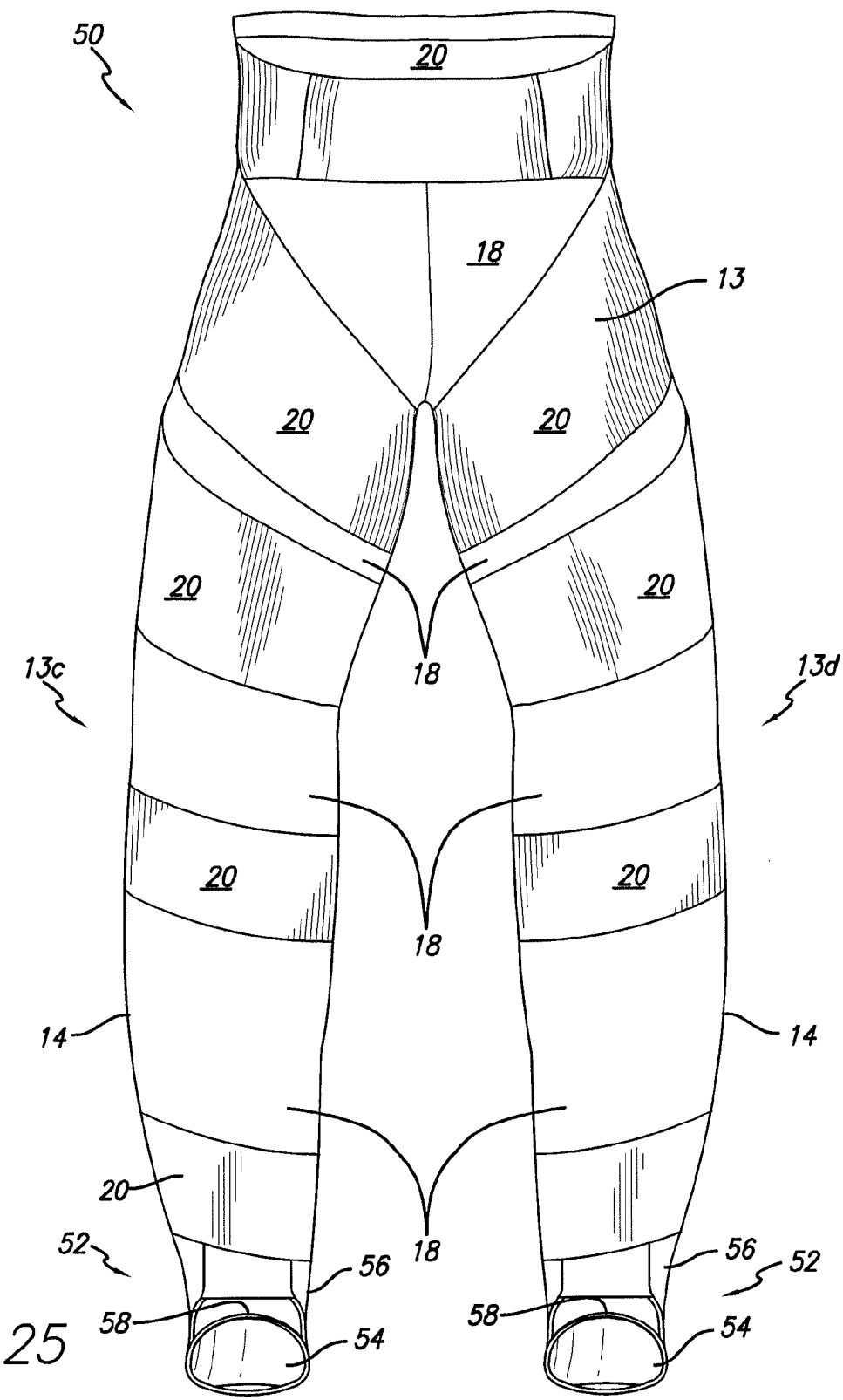
FIG. 25 is a front elevational view of the garment of FIG. 22 inside out and showing the grip layers on the inside thereof.
Figure 26:
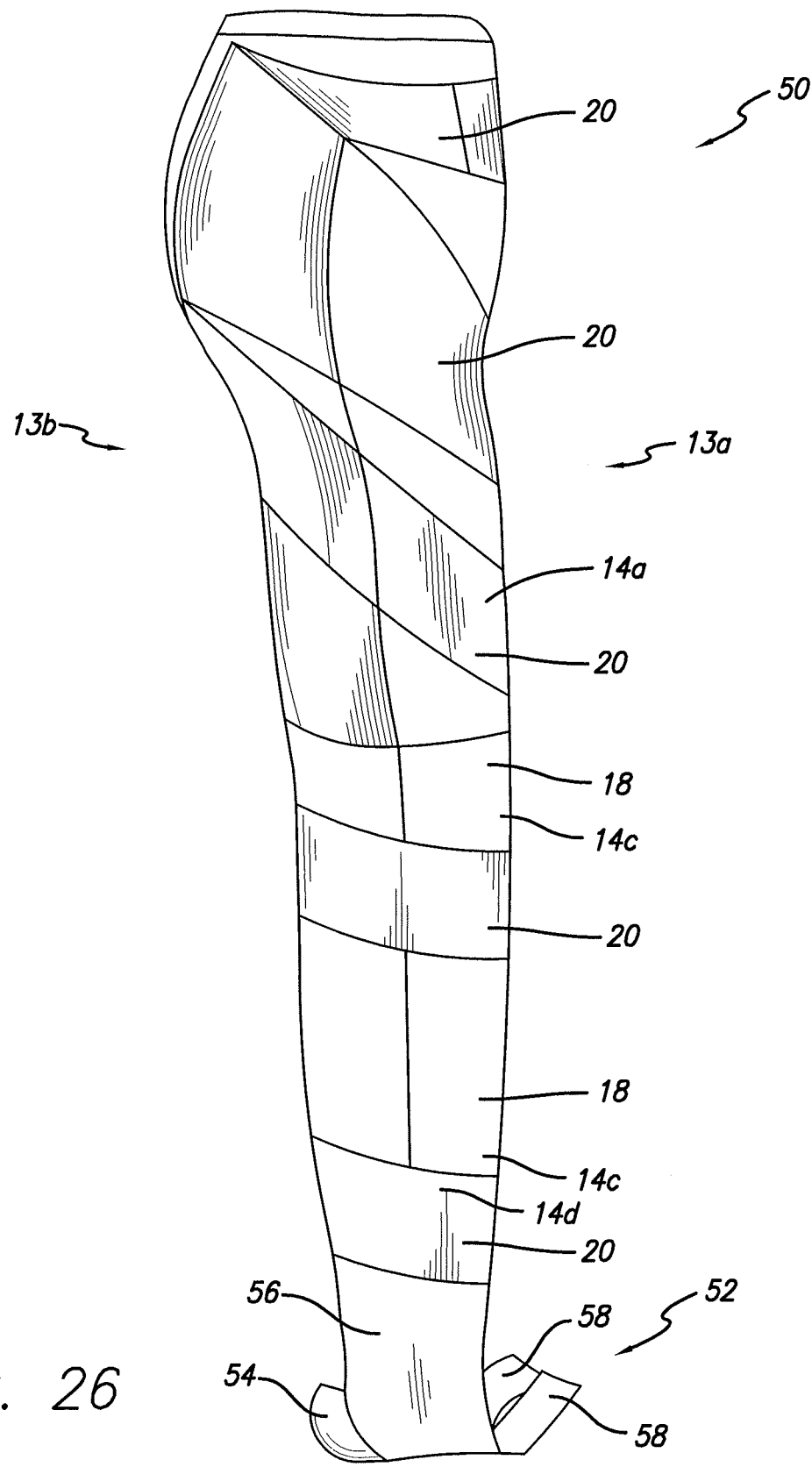
FIG. 26 is a right side elevational view of the garment of FIG. 22 inside out and showing the grip layers on the inside thereof.

FIGS. 22-32 show another preferred embodiment of a garment 50. In this embodiment of the present invention the garment 50 is a full length pair of pants that includes stirrups 52 that at least partially surround a wearer's foot. It will be understood that the majority of the garment 50 is the same as the garment 40 described above. Therefore, only the portion of the garment 50 that is different will be described. FIGS. 25-26 show the garment 50 inside-out to illustrate the preferred arrangement or pattern of the base grip layers 20.

Figure 22:
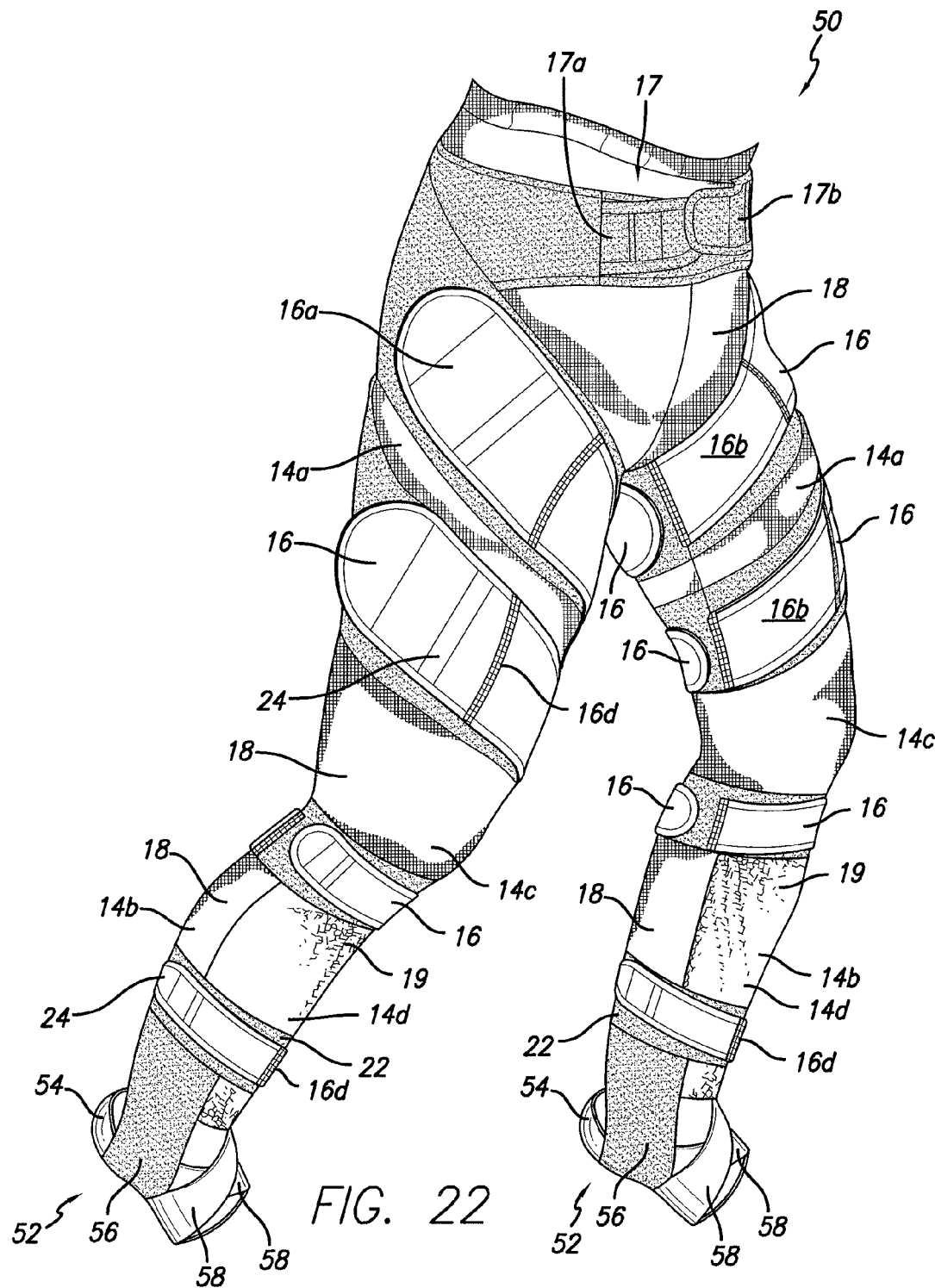
FIG. 22 is a perspective view of a garment (pants with stirrups) in accordance with another preferred embodiment of the present invention.

In a preferred embodiment, as shown in FIGS. 22-24, each leg portion 14 of the garment 50 includes a stirrup 52. The arch stirrup 52 supports and adds a suspension system that supports the wearer's heel (a natural fat pad) and the longitudinal and transverse arches of the foot. The support by the stirrup 52 elevates and stimulates the sensory motor system through the cutaneous nerve receptors in the bottom of the feet that are in numbers up to four times greater than most other parts of the human body.

As shown in FIG. 22 and the stirrup 52 preferably includes a heel support 54, a longitudinal arch support 56, a transverse arch support 58 and an adjustable arch strap 60. Together, these components all cooperate to define a space where the wearer's foot fits. The components of the stirrup 52 are preferably made of a grip material or layer, such as Fabrifoam®.

The longitudinal arch support 56 preferably mimics the function of a normal, toned posterior tibialis muscle that when functioning normally, naturally adds tone, support and lift to the longitudinal arch of the foot by lifting the arch from inferior to superior direction.

In a preferred embodiment, the heel support 54 preferably acts as a baffle to add support and continuity to the natural shock absorber in the heel of the foot. The heel support 54 creates a "fat pad dam" that allows the fat pad to stay full and not flatten out which helps the foot better absorb shock and pounding that occurs during very common abnormal gait patterns such as over pronating produces. Over time it is common for the natural ligamentous baffle to fail, causing the fat pad to compress, spread out and lose its shock absorbing capability. The heel support 54 helps control and concentrate the shape and efficacy of the pad so its function can be at its optimum.

In a preferred embodiment, the transverse arch support 58 includes two members that criss-cross as best shown in FIG. 22 The criss-cross pattern takes advantage of the spiral/helix features discussed above. The transverse arch support 58 supports under and across the midfoot at the transverse arch adding suspension and support of the foot during pronation, supination, inversion and eversion.

Figure 27:
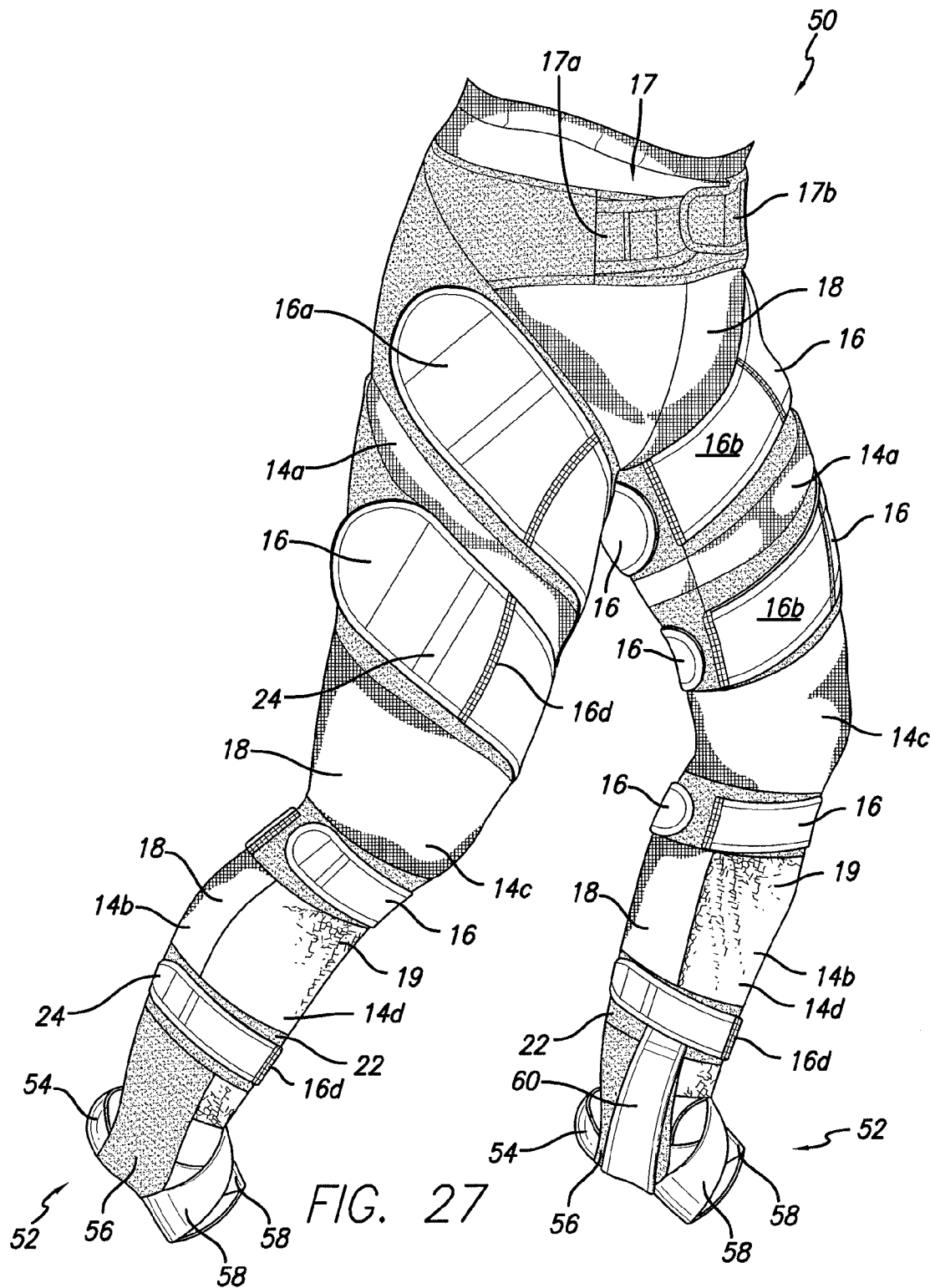
FIG. 27 is a perspective view of the garment of FIG. 22 with an adjustable arch strap shown on the left leg portion and stirrup.
Figure 28:
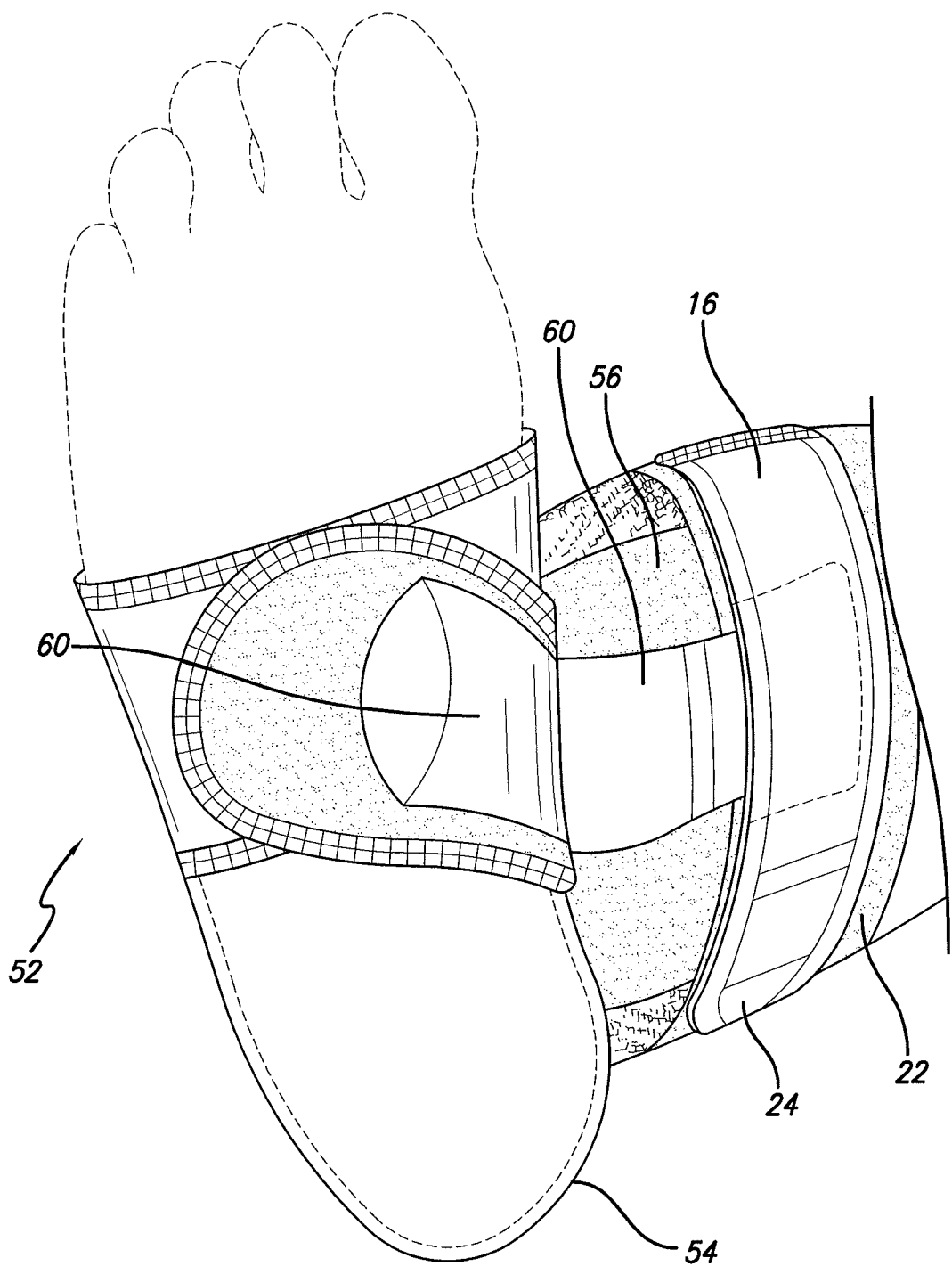
FIG. 28 is a bottom perspective view of the stirrup of the garment of FIG. 22 with the adjustable arch support.
Figure 29:
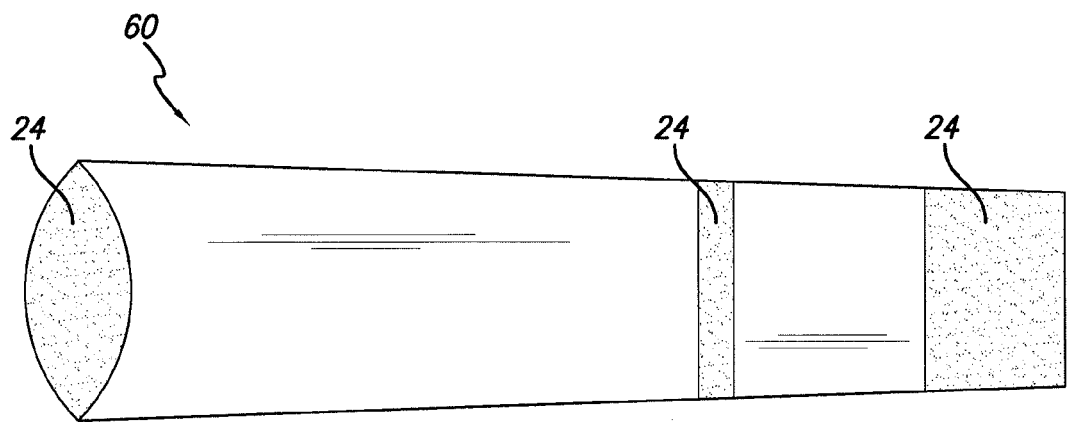
FIG. 29 is an elevational view of an adjustable arch strap.

The adjustable arch strap 60 (shown in FIGS. 27, 28 and 32) includes connectors 24 (preferably hook and loop tabs) at the opposite ends thereof. This allows the strap 60 to be connected at or near the shin straps 16 and the bottom of strap 60 is attached under the mid line of the longitudinal arch, as shown in FIGS. 27 and 28. The wearer can adjust the strap 60 based upon how much arch support the wearer desires. The further up the leg the strap 60 is attached, the more lift is accomplished. In a preferred embodiment, the strap 60 includes double anchors or connectors 24, as is shown in FIG. 29. However, this is not a limitation on the present invention. In use, the upper end of the strap 60 is preferably attached first and then the bottom or lower end of the strap 60 is attached under the longitudinal arch. In a preferred embodiment, the arch strap 60 is connected at or near the natural origin of the posterior tibialis. As shown in the figures, the longitudinal arch support 56 includes a connector layer 22 thereon for connecting the arch strap 60 as desired. It will be understood that the entire stirrup 52 can have a connector layer 22 on the outside thereof for connecting straps 60 as desired.

Figure 30:
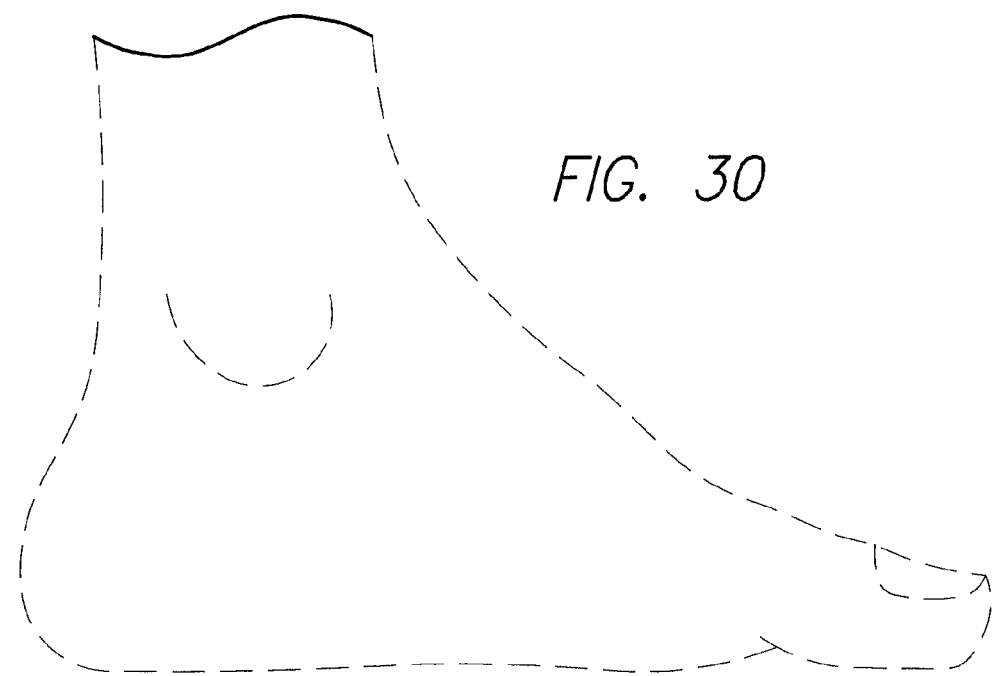
FIGS. 30-32 is a series of elevational views of a foot showing no support (FIG. 30), the support provided by a stirrup (FIG. 31) and the support provided by a stirrup combined with an adjustable arch strap (FIG. 32).
Figure 31:
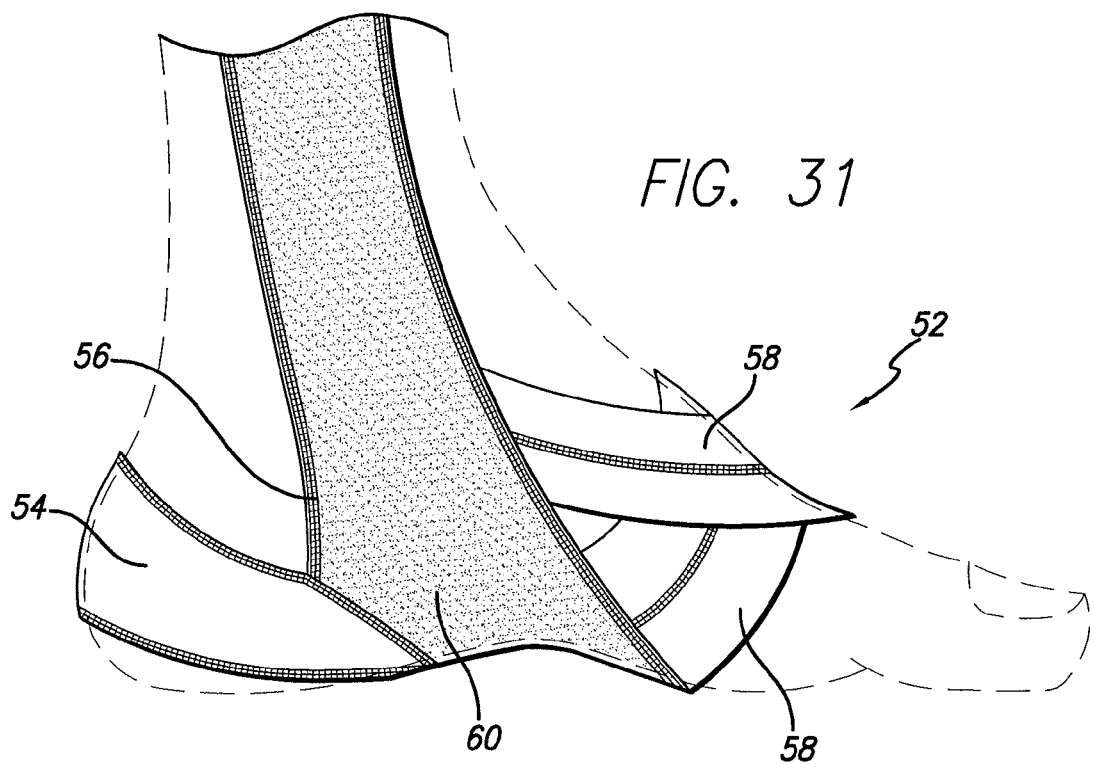
Figure 32:
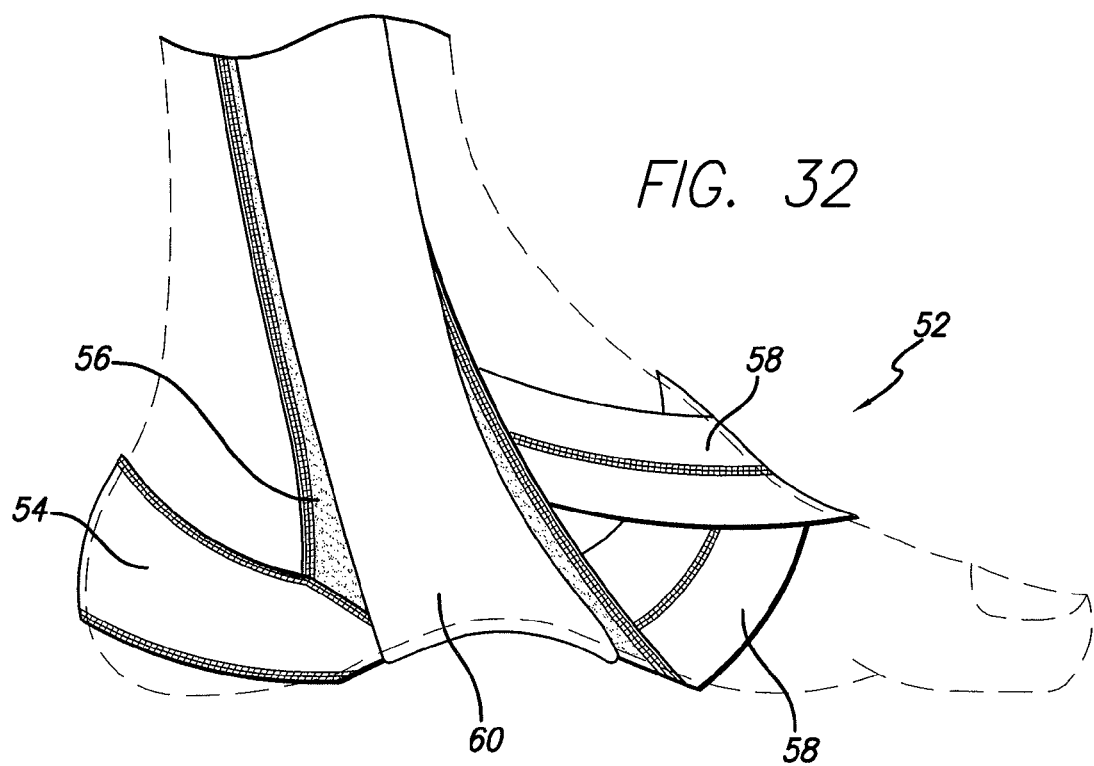

FIGS. 30-32 show a series of elevational views of a wearer's foot. FIG. 30 shows a foot without any support. This is a typical case of a flat arch with undertoned muscles. As can be seen in FIG. 31, using the stirrup 52, the arch support 56 provides support and lifts the arch of the foot. As shown in FIG. 32, the addition of the adjustable arch strap 60 provides even further lift and support to the arch of the foot. It will be appreciated that these figures show the stirrup without any Velcro or connector layer on the outside 22, except on the longitudinal arch support 56.

In the exemplary embodiments shown in the figures, the garments 10, 30, 40 and 50 are made of a plurality of pieces that are sewn together. It will be understood that the two-way stretch portions of the garments are made of Fabrifoam® with a layer of female hook and loop connector material on the opposite side. These are the grip and connector layers and are apparent by comparing the figures showing the outside of the garment to the figures showing the inside—the grip layers 20 correspond to the Velcro connector layers 22 (e.g., compare FIG. 2 to FIG. 6 or compare FIG. 3 to FIG. 8). The leg straps 16, ab straps 17, adjustable arch strap 60 and stirrup 52 are also made of this material. The 4-way stretch pieces or panels 18 are made of nylon. All of the pieces are sewn together to make the garment. It will be understood that this construction is only exemplary and not intended to be a limitation on the present invention.

Generally, in use, the stirrup 52 decreases over pronation, flat feet, serial distortion and/or other common mechanical and sensory motor muscular imbalances that can cause abnormal gait and movement pattern (wear and tear) pathology both locally in the lower extremities and globally, throughout the body's neuromusculoskeletal system. The stirrup 52 decreases stress on the joints by cuing proprioception and synchronizing the correct, optimal muscles and their firing patterns and retrains the muscles to better dynamically support structures that normally help displace weight and allow the wearer to move smoothly and efficiently. It will be understood that it is within the scope of the present invention to include any of the components of the stirrup 52 in various embodiments of the present invention. For example, only the longitudinal arch support may be included. In another embodiment, only the heel support may be included. In another embodiment, the adjustable arch strap may be permanently attached to the leg portion at one end.

Other embodiments may just include straps on the lower leg portions 14b. In other embodiments, viscoelastic tape can be disposed in certain portions of the garment for the purpose of preventing migration of the garment. Alternative means for providing a tacky surface for contacting the user's skin may also be used. It will understood that any combination of straps is within the scope of the present invention. In another embodiment, the garment may omit the straps and just include stirrups or may just include ab straps and stirrups.

In another preferred embodiment, the garment 10, 30, 40 or 50 may include neuro nubs, similar to those disclosed in the '704 publication. These neuro nubs preferably comprise soft, tacky bumps, or cutaneous nerve receptor stimulators, which are designed to provide a massaging, stimulating effect when the user moves. In general, patterns of such neuro nubs are helpful in creating proprioceptive stimulation, and also function to provide decreased migration of the garment as the body moves throughout its full range of motion. They are disposed at specific areas on the inside surface of the garment, to stimulate cutaneous nerve receptors in the skin and soft tissue structures to enhance "noise" that creates cues to the brain, enhancing muscle balance, body position awareness, posture, function, and performance.

Desired locations of the neuro nubs are at known acupuncture sites, as stimulation of these specific energy meridians enhances blood flow and stimulates normal physiology to organs and soft tissues that supply movement, support, and information crucial to those seeking optimal health and function. However, this is not a limitation on the present invention.

Conventional approaches to date have focused on mechanical support systems that have been shown to create atrophy and a reliance on a brace, which in the long term can create a system of dependence that the inventor believes is detrimental to optimal health and efficient recovery and performance. The straps together with the grip layers, create specific traction and tactile stimulation of cutaneous nerves in the skin. There are a minimum of 20,000 of such nerves per square inch of skin that will transfer specific information to the receptors (mechanoreceptors/nociceptors) that exist by the thousands/millions in the muscle, tendon, ligament, and joint surfaces, causing a predictable unloading of specific, predictable and common muscle imbalances that create and perpetuate joint stress and injury throughout the body.

Proprioceptive viscoelastic pads may optionally be employed in each of the illustrated embodiments, on the inside surface thereof, either permanently or releasably mounted thereto, for contacting the user's skin at strategic acupuncture meridian points or other locations in order to increase the proprioceptive effect of the garment. These pads, preferably made of silicone, have a skin-contacting surface which is grooved or otherwise modified to improve tactile response, using an acupuncture-type approach. The pressure generated by the garment 10, 30, 40 or 50 creates an acupressure effect. The strategic locations and numbers of pads may be varied in accordance with specific therapeutic objectives.

Essentially, the garment of the invention functions to create an exoskeleton for the user's lower body, thereby allowing for the sensory motor stimulation or proprioceptive awareness of strategic regions. Increased pressure is applied to these strategic body regions to perform the advantageous sensory motor stimulation or proprioceptive retraining or awareness. Prior art approaches involved mechanical treatment, i.e. physically manipulating portions of the body to desired configurations and limiting all range of motion including the healthy range of motion or non-injured muscles, which, over time, weakens muscles and makes the wearer dependent and decreases proprioception. This modern inventive approach instead induces a nervous system response through the application of strategic sensory motor stimulation and proprioceptive retraining and cuing and allows uninjured muscles to continue to move in the healthy range of motion, even during recovery. Accordingly, the garment provides advantageous effects for injured and uninjured wearers alike.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A garment adapted to be worn by a wearer, the garment comprising:
    a main body portion, wherein the main body portion is configured to be worn over at least a portion of the wearer's body, wherein the main body portion includes first and second portions each defining a longitudinal axis and configured to extend along a respective limb of the wearer so as to envelop a portion of a respective limb of the wearer,
    at least a first strap associated with the main body portion, wherein at least a portion of the first strap is releasably affixed to the main body portion,
    at least a first grip layer associated with the first portion, wherein the first strap overlies the first grip layer, and wherein the first grip layer is configured to come into contact with a wearer's skin when the garment is worn, and
    first and second abdominal straps associated with the main body portion, wherein the first and second abdominal straps each have a front surface and a back surface that have a connector thereon, whereby the first and second abdominal straps are configured to be connected with each other when the first abdominal strap is positioned at least partially over the second abdominal strap and when the second abdominal strap is positioned at least partially over the first abdominal strap.

2. The garment of claim 1, wherein the first strap is positioned such that it extends in a spiral about the longitudinal axis of the first portion.

3. The garment of claim 1, wherein the first strap has a first end that is permanently affixed to the main body portion and a second end that is temporarily affixed to the main body portion by a first connector.

4. The garment of claim 3, wherein the first strap includes a second connector located between the first connector and the second end.

5. The garment of claim 4, wherein the first and second connectors are hook and loop connectors and wherein the first portion includes corresponding hook and loop connectors for affixing the first and second connectors of the first strap to the first portion.

6. A method comprising the steps of:
    donning a garment that covers at least a portion of the wearer's body and at least a portion of the wearer's limb, wherein the garment includes first and second portions each defining a longitudinal axis and configured to extend toward a respective limb of the wearer so as to envelop a substantial portion of a respective upper portion of the respective limb, and the garment further includes first and second abdominal straps, the first and second abdominal straps each having a front surface and a back surface that have a connector thereon, whereby the first and second abdominal straps are configured to be connected with each other when the first abdominal strap is positioned at least partially over the second abdominal strap and when the second abdominal strap is positioned at least partially over the first abdominal strap,
    connecting the first and second abdominal straps with each other by positioning either the first abdominal strap at least partially over the second abdominal strap or the second abdominal strap at least partially over the first abdominal strap, and positioning a first strap on the first portion such that it extends in a spiral about the longitudinal axis of the first portion, thereby defining a first spiral direction, wherein the first strap overlies a first grip layer that is in contact with the skin on the wearer's limb, and wherein the first grip layer pulls the wearer's skin in the first spiral direction.

7. The method of claim 6, further comprising the step of positioning a second strap on the second portion such that it extends in a spiral about the longitudinal axis of the second portion, thereby defining a second spiral direction, wherein the second strap overlies a second grip layer that is in contact with the skin on the wearer's limb, and wherein the second grip layer pulls the wearer's skin in the second spiral direction.

8. The method of claim 7, wherein the first and second portions each include an upper portion and a lower portion, wherein the first and second straps are positioned on the upper portions of the first and second portions, respectively, wherein the method further comprises positioning third and fourth straps on the lower portions of the first and second portions, respectively, wherein the third and fourth straps are configured to overlie third and fourth grip layers that are in contact with the skin on the wearer's limb.

9. A garment adapted to be worn by a wearer, the garment comprising:
   a main body portion, wherein the main body portion is configured to be worn over at least a portion of the wearer's body, wherein the main body portion includes first and second portions each defining a longitudinal axis and configured to extend along a respective limb of the wearer so as to envelop a portion of a respective limb of the wearer,
   wherein each of the first and second portions includes one or more of:
      a strap releasably affixed to an upper leg portion of the garment,
      a strap releasably affixed to a lower leg portion of the garment, and
      a strap releasably affixed to a shin leg portion of the garment,
   wherein each of the first and second portions includes:
      a first grip layer located at the upper leg portion of the garment and configured to come into contact with a wearer's skin when the garment is worn, wherein the strap releasably affixed to the upper leg portion of the garment is configured to overlay at least partially the first grip layer located at the upper leg portion of the garment when the garment is worn.

10. A garment adapted to be worn by a wearer, the garment comprising:
    a main body portion, wherein the main body portion is configured to be worn over at least a portion of the wearer's body, wherein the main body portion includes first and second portions each defining a longitudinal axis and configured to extend along a respective limb of the wearer so as to envelop a portion of a respective limb of the wearer,
    wherein each of the first and second portions includes one or more of:
       a strap releasably affixed to an upper leg portion of the garment,
       a strap releasably affixed to a lower leg portion of the garment, and
       a strap releasably affixed to a shin leg portion of the garment,
    wherein each of the first and second portions includes:
       a first grip layer located at the lower leg portion of the garment and configured to come into contact with a wearer's skin when the garment is worn, wherein the strap releasably affixed to the lower leg portion of the garment is configured to overlay at least partially the first grip layer located at the lower leg portion of the garment when the garment is worn.

11. A garment adapted to be worn by a wearer, the garment comprising:
    a main body portion, wherein the main body portion is configured to be worn over at least a portion of the wearer's body, wherein the main body portion includes first and second portions each defining a longitudinal axis and configured to extend along a respective limb of the wearer so as to envelop a portion of a respective limb of the wearer,
    wherein each of the first and second portions includes one or more of:
       a strap releasably affixed to an upper leg portion of the garment,
       a strap releasably affixed to a lower leg portion of the garment, and
       a strap releasably affixed to a shin leg portion of the garment,
    wherein each of the first and second portions includes:
       a grip layer located at the shin portion of the garment and configured to come into contact with a wearer's skin when the garment is worn, wherein the strap releasably affixed to the shin portion of the garment is configured to overlay at least partially the grip layer located at the shin portion of the garment when the garment is worn.

12. The garment of claim 9, wherein each of the first and second portions includes:
    a second grip layer located at the upper leg portion and configured to come into contact with a wearer's skin when the garment is worn; and
    a second strap releasably affixed to the upper leg portion of the garment and configured to overlay at least partially the second grip layer when the garment is worn, the second strap distinct and separate from the strap releasably affixed to the upper leg portion of the garment.

13. The garment of claim 9, wherein each of the first and second portions includes:
    a second grip layer located at the lower leg portion and configured to come into contact with a wearer's skin when the garment is worn; and
    a second strap releasably affixed to the lower leg portion of the garment and configured to overlay at least partially the second grip layer when the garment is worn, the second strap distinct and separate from the strap releasably affixed to the upper leg portion of the garment.

14. The garment of claim 9, wherein each of the first and second portions includes:
    a second grip layer located at the shin portion and configured to come into contact with a wearer's skin when the garment is worn; and
    a second strap releasably affixed to the shin portion of the garment and configured to overlay at least partially the second grip layer when the garment is worn, the second strap distinct and separate from the strap releasably affixed to the upper leg portion of the garment.

15. The garment of claim 10, wherein each of the first and second portions includes:
- a second grip layer located at the shin portion and configured to come into contact with a wearer's skin when the garment is worn; and
- a second strap releasably affixed to the shin portion of the garment and configured to overlay at least partially the second grip layer when the garment is worn, the second strap distinct and separate from the strap releasably affixed to the lower leg portion of the garment.

16. The garment of claim 13, wherein each of the first and second portions includes:
- a third grip layer located at the shin portion and configured to come into contact with a wearer's skin when the garment is worn; and
- a third strap releasably affixed to the shin portion of the garment and configured to overlay at least partially the third grip layer when the garment is worn, the third strap distinct and separate from the second strap releasably affixed to the lower leg portion of the garment and the second strap.

17. A garment adapted to be worn by a wearer, the garment comprising:
- a main body portion, wherein the main body portion is configured to be worn over at least a portion of the wearer's body, wherein the main body portion includes first and second portions each defining a longitudinal axis and configured to extend along a respective limb of the wearer so as to envelop a portion of a respective limb of the wearer, wherein each of the first and second portions includes one or more of:
- a strap releasably affixed to an upper leg portion of the garment;
- a strap releasably affixed to a lower leg portion of the garment; and
- a strap releasably affixed to a shin leg portion of the garment, wherein each of the first and second portions includes two or more of:
- a heel support;
- a longitudinal arch support that includes two members arranged in a criss-cross pattern; and
- a transverse arch support configured to support under and across a midfoot region of the wearer.

18. The garment of claim 17, wherein each of the first and second portions includes an adjustable arch strap.

* * * * *